US009334536B2

(12) United States Patent
Van Eijk et al.

(10) Patent No.: US 9,334,536 B2
(45) Date of Patent: *May 10, 2016

(54) METHOD FOR HIGH-THROUGHPUT AFLP-BASED POLYMORPHISM DETECTION

(71) Applicant: Keygene N.V., Wageningen (NL)

(72) Inventors: Michael Josephus Theresia Van Eijk, Herpen (NL); Anker Preben Sørensen, Renkum (NL); Marco Gerardus Maria Van Schriek, Bennekom (NL)

(73) Assignee: Keygene N.V., Wageningen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/274,591

(22) Filed: May 9, 2014

(65) Prior Publication Data
US 2014/0295428 A1  Oct. 2, 2014

Related U.S. Application Data

(63) Continuation of application No. 13/666,385, filed on Nov. 1, 2012, now Pat. No. 8,815,512, which is a continuation of application No. 12/158,040, filed as application No. PCT/NL2006/000648 on Dec. 20, 2006, now Pat. No. 8,481,257.

(60) Provisional application No. 60/752,590, filed on Dec. 22, 2005.

(51) Int. Cl.
*C12Q 1/68* (2006.01)
*C12P 19/34* (2006.01)
*C40B 20/00* (2006.01)
*C07H 21/02* (2006.01)
*C07H 21/04* (2006.01)

(52) U.S. Cl.
CPC ............ *C12Q 1/6874* (2013.01); *C12Q 1/6827* (2013.01); *C12Q 1/6855* (2013.01); *C12Q 1/6869* (2013.01); *C12Q 1/6883* (2013.01); *C12Q 2600/156* (2013.01); *C12Q 2600/16* (2013.01)

(58) Field of Classification Search
CPC ........ C12Q 1/68; C12Q 1/6827; C12P 19/14; C07H 21/02
USPC ........... 435/6.1, 6.11, 6.12, 91.1, 91.2; 506/2; 536/23.1, 24.2, 24.3
See application file for complete search history.

(56) References Cited

U.S. PATENT DOCUMENTS

| | | | |
|---|---|---|---|
| 5,908,978 A | 6/1999 | Amerson et al. | |
| 5,955,276 A | 9/1999 | Morgante et al. | |
| 6,013,445 A | 1/2000 | Albrecht et al. | |
| 6,045,994 A | 4/2000 | Zabeau et al. | |
| 6,090,556 A | 7/2000 | Kato | |
| 6,100,030 A | 8/2000 | McCasky Feazel et al. | |
| 6,248,526 B1 | 6/2001 | Weimer | |
| 6,480,791 B1 | 11/2002 | Strathmann | |
| 6,534,293 B1 | 3/2003 | Barany et al. | |
| 6,887,666 B1 | 5/2005 | Hager | |
| 7,217,516 B2 | 5/2007 | Van Eijk et al. | |
| 7,220,549 B2 | 5/2007 | Buzby | |
| 7,300,751 B2 | 11/2007 | Li et al. | |
| 7,323,305 B2 | 1/2008 | Leamon et al. | |
| 7,935,488 B2 | 5/2011 | Zabeau et al. | |
| 8,614,073 B2 | 12/2013 | Van Eijk et al. | |
| 2002/0025532 A1 | 2/2002 | Huang et al. | |
| 2002/0106649 A1 | 8/2002 | Lizardi et al. | |
| 2002/0198371 A1 | 12/2002 | Wang | |
| 2003/0165923 A1 | 9/2003 | Li et al. | |
| 2003/0190645 A1 | 10/2003 | Van Eijk et al. | |
| 2004/0053236 A1 | 3/2004 | McCallum et al. | |
| 2004/0086912 A1 | 5/2004 | Luo et al. | |
| 2004/0157238 A1 | 8/2004 | Quinn et al. | |
| 2004/0185484 A1 | 9/2004 | Costa et al. | |
| 2004/0203032 A1 | 10/2004 | Lander et al. | |
| 2005/0064406 A1 | 3/2005 | Zabarovsky et al. | |
| 2005/0095645 A1 | 5/2005 | Jones et al. | |
| 2005/0130173 A1 | 6/2005 | Leamon et al. | |
| 2005/0153317 A1 | 7/2005 | DeNise et al. | |
| 2005/0233354 A1 | 10/2005 | Kennedy | |
| 2008/0032287 A1 | 2/2008 | Cantor et al. | |

(Continued)

FOREIGN PATENT DOCUMENTS

EP  0 534 858 A1  3/1993
EP  0 976 835     2/2000

(Continued)

OTHER PUBLICATIONS

454 Life Science, "Keygene Selects 454 Life Sciences' Novel Sequencing Technology to Enable Large-Scale SNP Discovery and Detection in Higher Eukaryotic Organisms," News & Events—Press Releases, 2006, pp. 1-2, [XP002452166], Internet: URl:http://www.454.com/news-events/press-releases.asp?display=detail&id=46.

(Continued)

*Primary Examiner* — Narayan Bhat
(74) *Attorney, Agent, or Firm* — Foley & Lardner LLP; Sunit Talapatra

(57) ABSTRACT

The invention relates to a method for the high throughput discovery, detection and genotyping of one or more genetic markers in one or more samples, comprising the steps of restriction endonuclease digest of DNA, adaptor-ligation, optional pre-amplification, selective amplification, pooling of the amplified products, sequencing the libraries with sufficient redundancy, clustering followed by identification of the genetic markers within the library and/or between libraries and determination of (co-)dominant genotypes of the genetic markers.

19 Claims, 6 Drawing Sheets

(56) References Cited

U.S. PATENT DOCUMENTS

| | | |
|---|---|---|
| 2008/0194418 A1 | 8/2008 | Johnson et al. |
| 2009/0142758 A1 | 6/2009 | Van Eijk et al. |
| 2009/0208943 A1 | 8/2009 | Van Eijk et al. |

FOREIGN PATENT DOCUMENTS

| | | |
|---|---|---|
| EP | 1 124 990 | 8/2001 |
| EP | 1 574 585 | 9/2005 |
| EP | 1 634 956 B1 | 3/2006 |
| JP | 2000-041687 | 2/2000 |
| JP | 2002-537855 | 11/2002 |
| JP | 2004-113241 | 4/2004 |
| JP | 2004-208586 | 7/2004 |
| JP | 2005-021149 | 1/2005 |
| WO | WO-93/06239 | 4/1993 |
| WO | WO-96/04393 | 2/1996 |
| WO | WO-98/51789 | 11/1998 |
| WO | WO 00/24939 | 5/2000 |
| WO | WO-00/53802 | 9/2000 |
| WO | WO 00/61800 | 10/2000 |
| WO | WO 00/61801 | 10/2000 |
| WO | WO-00/78945 | 12/2000 |
| WO | WO 01/38572 | 5/2001 |
| WO | WO-01/75167 A1 | 10/2001 |
| WO | WO-01/88189 | 11/2001 |
| WO | WO-03/012118 | 2/2003 |
| WO | WO-2004/022758 | 3/2004 |
| WO | WO 2005/003375 | 1/2005 |
| WO | WO-2005/065814 | 7/2005 |
| WO | WO 2006/137733 A | 12/2006 |
| WO | WO-2006/137734 | 12/2006 |
| WO | WO 01/21840 A2 | 3/2011 |

OTHER PUBLICATIONS

Altshuler, et al. "An SNP map of the human genome generated by reduced representation shotgun sequencing", Nature, Sep. 28, 2000, vol. 47, pp. 513-516.

Amos, Cl. et al., "DNA Pooling in Mutation Detection with Reference to Sequence Analysis", American Journal of Human Genetics, vol. 66, 2000, pp. 1689-1692.

Church, et al., "Multiplex DNA Sequencing", Research Articles, Science, vol. 240, Apr. 1988, pp. 185-188.

Colbert, T. et al., "High-Throughput Screening for Induced Point Mutations", Plant Physiology, vol. 126, 2001, pp. 480-484.

Fakhrai-Rad, H. et al., "Prosequencing: An Accurate Detection Platform for Single Nucleotide Polymorphisms", Human Mutation, vol. 19, pp. 479-485 (2002).

Gupta, et al. "Single nucleotide polymorphisms: A new paradigm for molecular marker technology and DNA polymorphism detection with emphasis on their use in plants." Current Science, Feb. 2001, vol. 80, No. 4, pp. 524-535.

Janssen, et al., "Application of Corps? Technology for SNP Marker Discovery in Maize," Plant & Animal Genomes XV Conference, 2007, p. 1 [XP002452171], Internet: URL:http://www.intl-pag.org/15/abstracts/PAG15_PO3e_183.html.

Lavebratt, C. et al., "Pyrosequencing-Based SNP Allele Frequency Estimation in DNA Pools", Human Mutation, vol. 23, pp. 92-97 (2004).

Qiu, F. et al., "DNA Sequence-Based 'Bar Codes' for Tracking the Origins of Expressed Sequence Tags from a Maize eDNA Library Constructed Using Multiple mRNA Sources", Plant Physiology, 133:475-481, Oct. 2003.

Solexa, "Application Note: DNA sequencing," 2006, pp. 1-2, [XP002452169], Internet: URL:http://www.fasteris.com/pdf/DNASeq_AppNote_10_5_06.pdf.

Sood, et al., Method for reverse genetic screening in zebrafish by resequencing and TILLING, Methods, vol. 29, 2006, pp. 220-227.

Stemple, D.L., "TILLING—a high-throughput harvest for functional genomics", Nature Reviews, vol. 5, pp. 1-6 (2004).

Till, et al. "Large-scale discovery of induced point mutations with high-throughput TILLING." Genome Research, Mar. 2003, vol. 13, No. 3, pp. 524-530.

van Eijk, et al., "Complexity Reduction of Polymorphic Sequences (CRoPS): A Novel Approach for High Throughput Polymorphism Discovery," Plant and Animal Genomes XIV Conference, 2006, p. 1, [XP002452165], Internet: URL:http://www.intl-pag.org/14/abstracts/PAG14_W410.html.

van Eijk, et al., "Sequence-Based AFLP® Detection Using Solexa's Clonal Single Molecule Array (CSMA?) Technology," Plant & Animal Genomes XV Conference, 2007, p. 1, [XP002452170], Internet: URL:http://www.intl-pag.org/15/abstracts/PAG15_P02c_69.html.

Vandenbussche, et al. "Toward the analysis of the petunia MADS box gene family by reverse and forward transposon insertion mutagenesis approaches: B, C, and D floral organ identify functions require SEPALLATA-like MADS box genes in petunia." The Plant Cell, Nov. 2003, vol. 15, No. 11, pp. 2680-2693.

Vieux, E. F. et al., "Primer Design for PCR and Sequencing in High-Throughput Analysis of SNPs", BioTechniques, vol. 32, pp. S28-S32 (2002).

Wineholds, et al. "Efficient Target-selected mutagenesis in zebrafish." Genome Research, Dec. 2003, vol. 13, No. 12, pp. 2700-2707.

Wineholds, et al. "Target-selected gene inactivation in zebrafish.", Methods in Cell Biology, 2004, vol. 77, pp. 69-90.

World's Technology News, "Solexa to Conduct Technology Seminar at the American Society of Human Genetics Conference", 2005, p. 1, [XP002452168], Internet: URL:http://www.mirror99.com/20051028/solexa_to_conduct_technology_seminar_at_the_american_society_of_human_genetics_bhfd.jspx.

The English Translation of the Office Action received in the related Japanese Patent Application No. JP 2008-547127, dated Dec. 5, 2012.

Accelerated Examination Support Document, filed in the USPTO on Oct. 5, 2010 in U.S. Appl. No. 12/484,541.

Baird, et al., "Rapid SNP Discovery and Genetic Mapping Using Sequenced RAD Markers", PLoS ONE, Oct. 2008, vol. 3, issue 10, e3376, pp. 1-7.

Breyne, et al., "Transcriptome analysis during cell division in plants", Proceedings of the National Academy of Sciences, Nov. 2002, vol. 99, No. 23, pp. 14825-14830.

The Search Report received in the corresponding European Patent Application No. 10186841.2, dated Aug. 5, 2011.

Fujiki et ai, Genetic evidence for CFTR dysfunction in Japanese: background for chronic pancreatitis, 2004, J Med Genet, 41, e55, pp. 1-6.

International Search Report for International PCT Application No. PCT/NL2006/000648, dated May 14, 2007 (4 pgs).

Lewis, et al., "High-Density Detection of Restriction-Site-Associated DNA Markers for Rapid Mapping of Mutated Loci in Neurospora", Genetics, Oct. 2007, vol. 177, pp. 1163-1171.

Lindstedt, et al., "A variation of the amplified-fragment length polymorphism (AFLP) technique using three restriction endonucleases, and assessment of the enzyme combinatyion BgIII-MfeI for AFLP analysis of Salmonella enterica subs . enterica isolates", Fems Microbiology Letters, vol. 189, No. 1, pp. 19-24.

Lizardi et ai, Mutation detection and single-molecule counting using isothermal rolling-circle amplification, 1998, Nature Genetics, 19, 225-232.

Margulies, et al., "Genome sequencing in microfabricated high-density picolitre reactors", Nature, Sep. 2005, vol. 437, No. 7057, pp. 376-380.

Marth et al, A general approach to single-nucleotide polymorphism discovery, 1999, Nature Genetics, 23, 452-456.

Meksem, K., et al., "Conversion of AFLP bands into high-throughput DNA markers," Mol Genet Genomics, 2001, pp. 207-214, vol. 265, [XP-002652268].

Miller, et al., "RAD marker microarrays enable rapid mapping of zebrafish mutations", Genome Biology, 2007, vol. 8, Issue 6, Article R105.

Miller, et al., "Rapid and cost-effective polymorphism identification and genotyping using restriction site associated DNA (RAD) markers", Genome Research, 2007, vol. 17, pp. 240-248.

(56) References Cited

OTHER PUBLICATIONS

Nakai et al, Highly MUltiplexed Genotyping of Coronary Artery Disease-Associated SNPs Using MALDI-TOF Mass Spectrometry, 2002, Human Mutation, 20,133-138.
Nicod, et al., "SNPs by AFLP (SBA): a rapid SNP isolation strategy for non-model organisms", *Nucleic Acids Research*, Mar. 2003, vol. 31, No. 5, pp. E19-1-E19-5.
Reijans, et al., "Quantitative Comparison of cDNA-AFLP, Microarrays, and GeneChip Expression Data in *Saccharomyces cerevisiae*," Genomics, 2003, vol. 82, pp. 606-618.
Shendure, et al., "Accurate multiplex polony sequencing of an evolved bacterial genome", *Science*, Sep. 2005, vol. 309, No. 5741, pp. 1728-1732.
Simko, Ivan., "One potato, two potato: haplotype association mapping in autotetraploids", *Trends in Plant Science*, 2004, vol. 9, No. 9, pp. 441-448. *(Color Reference)*.
Vos, P., et al., "AFLP: a new technique for DNA fingerprinting," *Nucleic Acids Research*, 1995, pp. 4407-4414, vol. 23, No. 21, [XP-00093921].
U.S. Appl. No. 90/013,467, filed Mar. 13, 2015, Cornell University.
Bishop, et al. "Analysis of the transcriptome of the protozoan Theileria parva using MPSS reveals that the majority of genes are transcriptionally active in the schizont stage", Nucleic Acids Research, 2005, vol. 33, No. 17, pp. 5503-5511.
Dong, et al. "Flexible Use of High-Density Oligonucleotide Arrays for Single-Nucleotide Polymorphism Discovery and Validation", Genome Research, 2001, vol. 11, No. 8, pp. 1418-1424.
EP Search Report in EP Appln No. 10 18 4351 dated Jan. 28, 2011.
First Examination Report in India Appln No. 1142/KOLNP/2008 dated Feb. 17, 2014.
Gruber, et al. "Estimation of single nucleotide polymorphism allele frequency in DNA pools by using Pyrosequencing", Hum Genet (2002), vol. 110, pp. 395-401.
Henikoff, et al. "TILLING. Traditional Mutagenesis Meets Functional Genomics", Plant Physiology, Jun. 2004, vol. 135, pp. 630-636.
International Search Report in PCT/NL2006/000312 dated Sep. 28, 2006.
International Search Report in PCT/NL2006/000467, mailed Mar. 26, 2007.
Iwahana, et al. "T-cassette Ligation: A Method for Direct Sequencing and Cloning of PCR-amplified DNA Fragments", PCR Methods and Applications, 1994, pp. 219-224.
Jordan, et al. "Genome complexity reduction for SNP genotyping analysis", PNAS, Mar. 5, 2002, vol. 99, No. 5, pp. 2942-2947.
Lehninger, "The Principles of Biochemistry", The Johns Hopkins University School of Medicine, Nov. 1982, Table of Contents.
Li et al., "A fast neutron deletion mutagenesis-based reverse genetics system for plants", The Plant Journal, 2001, vol. 27, No. 3, pp. 235-242.
McCallum et al., "Targeting Induced LocalLesions INGenomes (TILLING) for Plant Functional Genomics", Plant Physiology (2000), vol. 123, No. 2, pp. 439-442.
McCallum, et al., "Targeted Screening for Induced Mutations", Nature Biotechnology (Apr. 2000), vol. 18, No. 4, pp. 455-457.

Meyers, et al. "Analysis of the transcriptional complexity of Arabidopsis thaliana by massively parallel signature sequencing", Nature Biotechnology, Aug. 2004, vol. 22, No. 8, pp. 1006-1011.
Mueller, et al. "AFLP genotyping and fingerprinting", Tree (Oct. 1999), vol. 14, No. 10, pp. 389-394.
Nair, et al. "PCR-based DNA markers linked to a gall midge resistance gene, Gm4t, has potential for marker-aided selection in rice", Theor Appl Genet (1996), vol. 92, pp. 660-665.
Office Action in JP Appln No. 2008-518056 dated Jun. 27, 2012.
Office Action in JP Appln No. 2013-006095 dated Jul. 2, 2014.
Partial EP Search Report in EP Appln No. 10 07 5564 dated Feb. 8, 2011.
Protest Under Section 34.1 of the Patent Act in CA Appln No: 2,623,539 on May 8, 2014.
Retrieved from EBI accession No. UNIPROT:C5Z1DO, Sep. 1, 2009, "RecName: Full=Pectinesterase; EC=3.1.1.11;".
Retrieved from EBI accession No. UNIPROT:Q8VYZ3, Mar. 1, 2002, "RecName: Full=Probable pectinesterase 53; Short=PE 53; EC=3.1.1.11; AltName: Full=Pectin methylesterase 53; short-AtPME53; Flags: Precursor."
Swindell, "The Association Among Gene Expression Responses to Nine Abiotic Stress Treatments in Arabidopsis thaliana", Genetics, Dec. 2006, vol. 1811-1824.
Volkmuth, et al. "Technical Advances: Genome-Wide cDNA-AFLP Analysis of the Arabidopsis Transcriptome", A Journal of Integrative Biology, 2003, vol. 7, No. 2, pp. 143-160.
Wienholds, et al. "Target-Selected Inactivation of the Zebrafish rag1 Gene", Science (2002), vol. 297, pp. 99-102.
Wolford, et al., "High-throughput SNP detection by using DNA pooling and denaturing high performance liquid chromatography (DHPLC)", Human Genetics (2000) vol. 107, pp. 83-487.
Yuanxin, et al. "T-linker-specific ligation PCR (T-linker PCR): an advanced PCR technique for chromosome walking or for isolation of tagged DNA ends", Nucleic Acids Research, 2003, vol. 31, No. 12, e68, 7 pgs.
Bensch, et al. "Ten years of AFLP in ecology and evolution: why so few animals?", Molecular Ecology, Sep. 2005, vol. 14, Issue 10, pp. 2899-2914.
Communication (EP Search Report) in EP AppLn No. 10186841.2 dated Aug. 5, 2011.
Data sheet Dral, download from the internet, http://www.neb.com/nebecomm/products, printed on Dec. 18, 2010, p. 1.
Griffin, et al. "Single-nucleotide polymorphism analysis by MALDI-TOF mass spectrometry", TIBTECH, Feb. 2000, vol. 18, pp. 77-84.
Nelson, et al. "Complete Genome Sequence of the Oral Pathogenic Bacterium Porphyromonas gingivalis Strain W83", Journal of Bacteriology, Sep. 2003, pp. 5591-5601.
Sallaud, et al. "Highly efficient production and characterization of T-DNA plants for rice (*Oryza sativa* L.) functional genomics", Theor Appl Genet, 2003, vol. 106, pp. 1396-1408.
Savelkoul, et al. "Amplified-Fragment Length Polymorphism Analysis: the State of an Art", Journal of Clinical Microbiology, 1999, vol. 37, No. 10, pp. 3083-3091.
Truong et al, "Sequence-Based Genotyping for Marker Discovery and Co-Dominant Scoring in Germplasm and Populations," May 2012, PLoS One, vol. 7, No. 5, e37565, pp. 1-9.
Van Der Meulen, et al. "Highly automated AFLP fingerprint analysis on the MegaBACE capillary sequencer", Plant, Animal & Microbe Genomes X Conference, Jan. 12-16, 2002, p. 228, pp. 135.

```
    Primer set I used for preamplification of PSP-11
E01LKRS1 5'-CGTCAGACTGCGTACCAATTCA-3'

M15KKRS1 5'-TGGTGATGAGTCCTGAGTAACA-3'

Primer set II used for preamplification of PI201234
E01LKRS2 5'-CAAGAGACTGCGTACCAATTCA-3'

M15KKRS2 5'-AGCCGATGAGTCCTGAGTAACA-3'
```

Figure 2
DNA quality control on a 1% agarose gel
DNA concentration measured with the Nanodrop
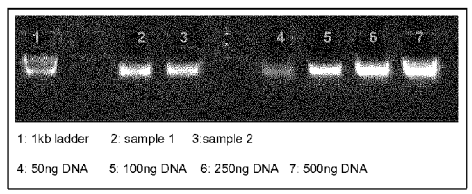
Figure 2A. Short gel electrophoresis
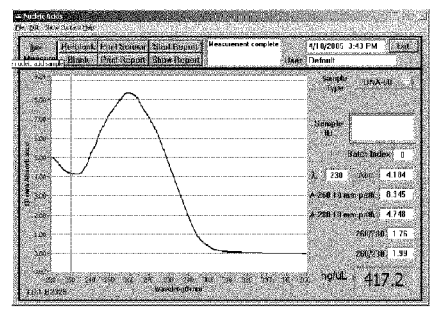
Figure 2C. Concentration sample 1.
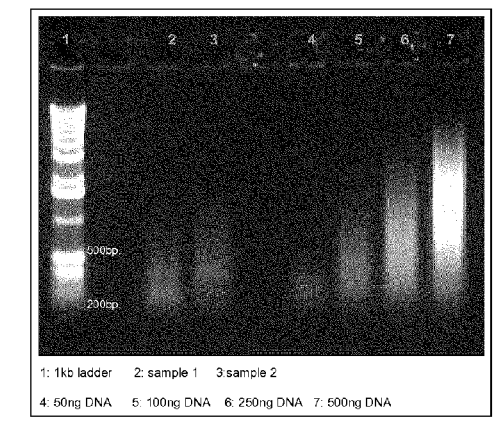
Figure 2B. Long gel electrophoresis
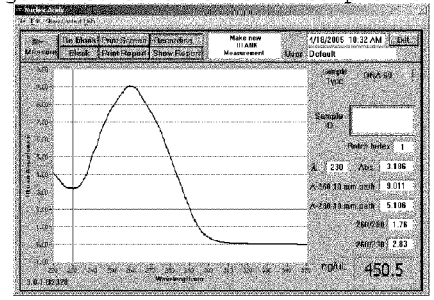
Figure 2D Concentration sample 2

DNA quality control on a 1% agarose gel

DNA concentrations measured on the Nanodrop

Figure 3A. Short gel electrophoresis

| Nr. | Sample ID | ng/uL | A260 | 260/280 | 260/230 | Constant |
|---|---|---|---|---|---|---|
| 1 | P1.1 | 22.61 | 0.452 | 1.5 | 1.81 | 50 |
| 2 | P1.2 | 19.08 | 0.382 | 1.67 | 2.49 | 50 |
| 3 | P1.3 | 18.05 | 0.361 | 1.63 | 2.35 | 50 |
| 4 | P1.4 | 15.19 | 0.304 | 1.71 | 2.1 | 50 |

| Nr. | Sample ID | ng/uL | A260 | 260/280 | 260/230 | Constant |
|---|---|---|---|---|---|---|
| 5 | P2.1 | 17.5 | 0.35 | 1.66 | 2.01 | 50 |
| 6 | P2.2 | 16.67 | 0.333 | 1.96 | 2 | 50 |
| 7 | P2.3 | 22.03 | 0.441 | 1.81 | 2.28 | 50 |
| 8 | P2.4 | 9.8 | 0.196 | 1.78 | 1.98 | 50 |

Figure 3B. Long gel electrophoresis

Figure 4A. Sequence data processing pipeline
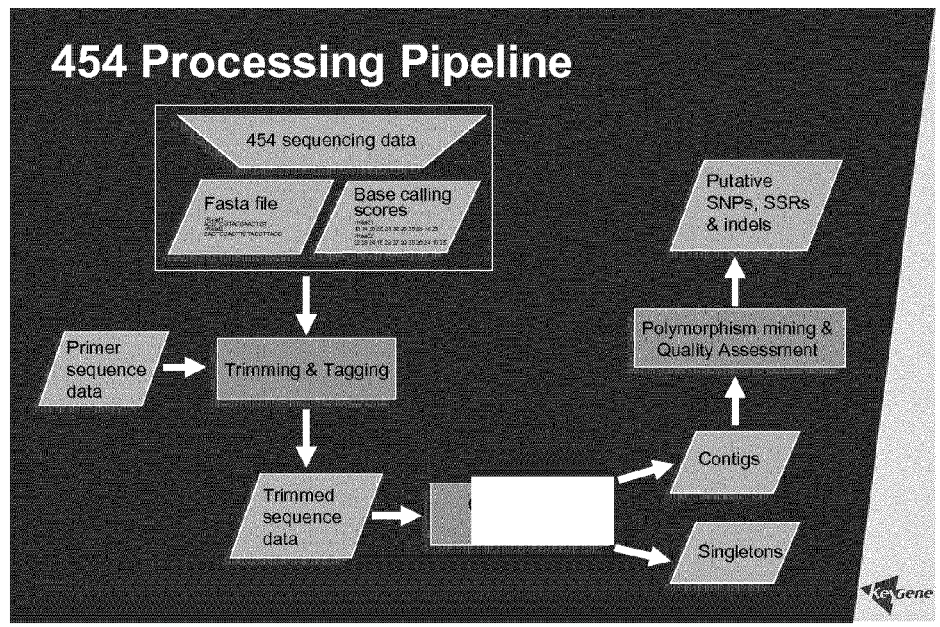
Figure 4B. Polymorphism mining and quality assignment process
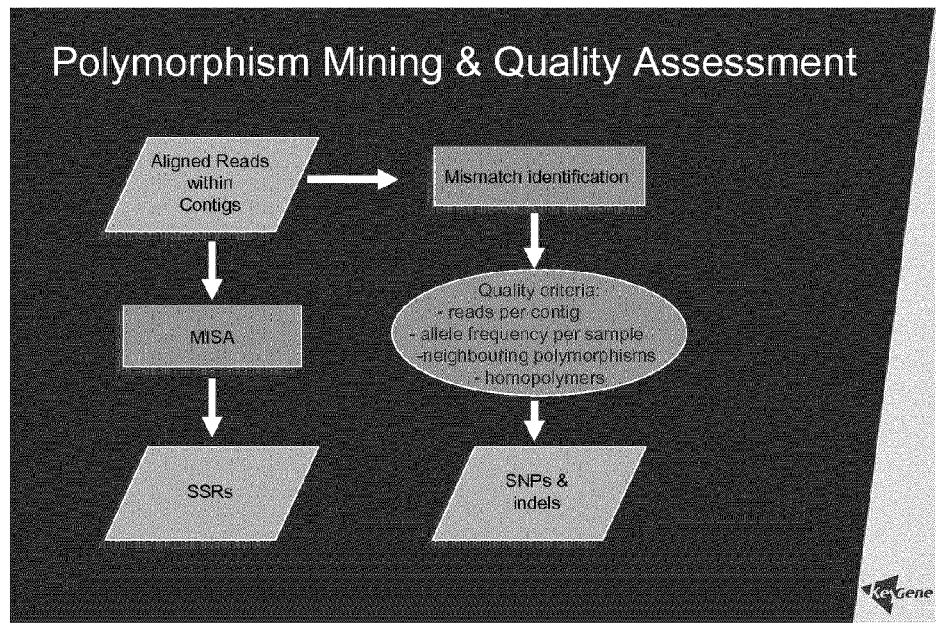

SEQUENCE LISTING

```
<160> NUMBER OF SEQ ID NOS: 43

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgtcagactg cgtaccaatt ca                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tggtgatgag tcctgagtaa ca                                              22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caagagactg cgtaccaatt ca                                              22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agccgatgag tcctgagtaa ca                                              22

<210> SEQ ID NO 5
```

<211> LENGTH: 17
<212> TYPE: DNA
<213> ORGANISM: Artificial Sequence
<220> FEATURE:
<223> OTHER INFORMATION: Description of Artificial Sequence: Synthetic
      adaptor oligonucleotide

<400> SEQUENCE: 5
ctcgtagact gcgtacc                                                    17

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      adaptor oligonucleotide

<400> SEQUENCE: 6
aattggtacg cagtctac                                                   18

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      adaptor oligonucleotide

<400> SEQUENCE: 7
gacgatgagt cctgag                                                     16

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: Synthetic
      adaptor oligonucleotide

<400> SEQUENCE: 8
tactcaggac tcat                                                       14

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      adaptor oligonucleotide

<400> SEQUENCE: 9
agactgcgta ccaattca                                                   18

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gatgagtcct gagtaac                                                    17

<210> SEQ ID NO 11
<211> LENGTH: 22

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgtcagactg cgtaccaatt ca                                              22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
caagagactg cgtaccaatt ca                                              22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tggtgatgag tcctgagtaa ca                                              22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agccgatgag tcctgagtaa ca                                              22

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gactgcgtac caattcaac                                                  19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gatgagtcct gagtaacag                                                  19

<210> SEQ ID NO 17
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 17
acgtgtagac tgcgtaccga aa                                                  22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acgtgatgag tcctgagtaa ca                                                  22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgtagtagac tgcgtaccga ac                                                  22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cgtagatgag tcctgagtaa ca                                                  22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtacgtagac tgcgtaccga ag                                                  22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtacgatgag tcctgagtaa ca                                                  22

<210> SEQ ID NO 23
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 23
tacggtagac tgcgtaccga at                                              22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tacggatgag tcctgagtaa ca                                              22

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agtcgtagac tgcgtaccga aa                                              22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
agtcgatgag tcctgagtaa ca                                              22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
catggtagac tgcgtaccga ac                                              22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
catggatgag tcctgagtaa ca                                              22

<210> SEQ ID NO 29
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 29
gagcgtagac tgcgtaccga ag                                              22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gagcgatgag tcctgagtaa ca                                              22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgatgtagac tgcgtaccga at                                              22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tgatgatgag tcctgagtaa ca                                              22

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aaacccaaac tcccccaatc                                                 20

<210> SEQ ID NO 34
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agcggataac aatttcacac aggacatcag tagtcacact ggtacaaaaa tagagcaaaa     60
cagtagtg                                                              68

<210> SEQ ID NO 35
<211> LENGTH: 91
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 35
aaacccaaac tcccccaatc gatttcaaac ctagaacaat gttggttttg gtgctaactt     60
caaccccact actgttttgc tctattttg t                                     91

<210> SEQ ID NO 36
<211> LENGTH: 90
<212> TYPE: DNA
<213> ORGANISM: Artificial Sequence
<220> FEATURE:
<223> OTHER INFORMATION: Description of Artificial Sequence: Synthetic
      PI-201234 SNP containing oligonucleotide

<400> SEQUENCE: 36
aaacccaaac tcccccaatc gatttcaaac ctagaacagt gttggttttg gtgctaactt     60
caaccccact actgttttgc tctattttg                                       90

<210> SEQ ID NO 37
<211> LENGTH: 90
<212> TYPE: DNA
<213> ORGANISM: Artificial Sequence
<220> FEATURE:
<223> OTHER INFORMATION: Description of Artificial Sequence: Synthetic
      PI-201234 SNP oligonucleotide

<400> SEQUENCE: 37
aaacccaaac tcccccaatc gatttcaaac ctagaacagt gttggttttg gtgctaactt     60
caaccccact actgttttgc tctattttg                                       90

<210> SEQ ID NO 38
<211> LENGTH: 106
<212> TYPE: DNA
<213> ORGANISM: Artificial Sequence
<220> FEATURE:
<223> OTHER INFORMATION: Description of Artificial Sequence: Synthetic
      consensus polynucleotide

<400> SEQUENCE: 38
taacacgact ttgaacaaac ccaaactccc ccaatcgatt tcaaacctag aacartgttg     60
gttttggtgc taacttcaac cccactactg ttttgctcta tttttg                   106

<210> SEQ ID NO 39
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (33)..(33)
<223> OTHER INFORMATION: a, c, t, g, unknown or other

<400> SEQUENCE: 39
ttaacacgac tttgaacaaa cccaaactcc ccnaatcgat ttcaaaccta gaacaatgtt     60
ggttttggtg ctaacttcga ccccactact gttttgctct attttg                   107

<210> SEQ ID NO 40
<211> LENGTH: 107
<212> TYPE: DNA
<213> ORGANISM: Artificial Sequence
```

```
<220> FEATURE:
<223> OTHER INFORMATION: Description of Artificial Sequence: Synthetic
      polynucleotide
<220> FEATURE:
<221> NAME/KEY: modified_base
<222> LOCATION: (33)..(33)
<223> OTHER INFORMATION: a, c, t, g, unknown or other

<400> SEQUENCE: 40
ttaacacgac tttgaacaaa cccaaactcc ccnaatcgat ttcaaaccta gaacaatgtt      60
ggttttggtg ctaacttcaa ccccactact gttttgctct attttg                    107

<210> SEQ ID NO 41
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
ttaacatgac tttgaacaaa cccaaactcc cccaatcgat ttcaaaccta gaacagtgtt      60
ggttttggtg ctaacttcaa ccccactact gttttgctct a                         101

<210> SEQ ID NO 42
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
ttaacatgac tttgaacaaa cccaaactcc cccaatcgat ttcaaaccta gaacagtgtt      60
ggttttggtg ctaacttcaa cccactactg tttgtctcta                           100

<210> SEQ ID NO 43
<211> LENGTH: 107
<212> TYPE: DNA
<213> ORGANISM: Artificial Sequence
<220> FEATURE:
<223> OTHER INFORMATION: Description of Artificial Sequence: Synthetic
      consensus polynucleotide

<400> SEQUENCE: 43
ttaacacgac tttgaacaaa cccaaactcc cccaatcgat ttcaaaccta gaacaatgtt      60
ggttttggtg ctaacttcaa ccccactact gttttgctct attttg                    107
```

METHOD FOR HIGH-THROUGHPUT AFLP-BASED POLYMORPHISM DETECTION

This application is a Continuation of U.S. patent application Ser. No. 13/666,385, filed Nov. 1, 2012 which is a Continuation of U.S. patent application Ser. No. 12/158,040, filed Oct. 9, 2008, which is the U.S. National Stage Application of PCT/NL2006/000648, filed Dec. 20, 2006, which claims the benefit of U.S. Provisional Application No. 60/752,590, filed Dec. 22, 2005, all of which are incorporated by reference in their entirety.

SEQUENCE LISTING

The instant application contains a Sequence Listing which has been submitted in ASCII format via EFS-Web and is hereby incorporated by reference in its entirety. Said ASCII copy, created on Sep. 18, 2013, is named 085342-0306_SL.txt and is 11,333 bytes in size.

TECHNICAL FIELD

The present invention relates to the fields of molecular biology and genetics. The invention relates to rapid discovery, detection and large-scale genotyping of polymorphisms in a nucleic acid sample or between samples. The identified polymorphisms may be used as genetic markers.

BACKGROUND OF THE INVENTION

Exploration of genomic DNA has long been desired by the scientific, in particular medical, community. Genomic DNA holds the key to identification, diagnosis and treatment of diseases such as cancer and Alzheimer's disease. In addition to disease identification and treatment, exploration of genomic DNA may provide significant advantages in plant and animal breeding efforts, which may provide answers to food and nutrition problems in the world.

Many diseases are known to be associated with specific genetic components, in particular with polymorphisms in specific genes. The identification of polymorphisms in large samples such as genomes is at present a laborious and time-consuming task. However, such identification is of great value to areas such as biomedical research, developing pharmacy products, tissue typing, genotyping and population studies.

Markers, i.c. genetic markers, have been used for a very long time as a genetic typing method, i.e. to connect a phenotypic trait to the presence, absence or amount of a particular part of DNA (gene). One of the most versatile genetic typing technologies is AFLP, already around for many years and widely applicable to any organism (for reviews see Savelkoul et al. J. Clin. Microbiol, 1999, 37(10), 3083-3091; Bensch et al. Molecular Ecology, 2005, 14, 2899-2914)

The AFLP technology (Zabeau & Vos, 1993; Vos et al., 1995) has found widespread use in plant breeding and other field since its invention in the early nineties. This is due to several characteristics of AFLP, of which the most important is that no prior sequence information is needed to generate large numbers of genetic markers in a reproducible fashion. In addition, the principle of selective amplification, a cornerstone of AFLP, ensures that the number of amplified fragments can be brought in line with the resolution of the detection system, irrespective of genome size or origin.

Detection of AFLP fragments is commonly carried out by electrophoresis on slab-gels (Vos et al., 1995) or capillary electrophoresis (van der Meulen et al., 2002). The majority of AFLP markers scored in this way represent (single nucleotide) polymorphisms occurring either in the restriction enzyme recognition sites used for AFLP template preparation or their flanking nucleotides covered by selective AFLP primers. The remainder of the AFLP markers are insertion/deletion polymorphisms occurring in the internal sequences of the restriction fragments and a very small fraction on single nucleotide substitutions occurring in small restriction fragments (<approximately 100 bp), which for these fragments cause reproducible mobility variations between both alleles; these AFLP markers can be scored co-dominantly without having to rely on band intensities.

In a typical AFLP fingerprint, the AFLP markers therefore constitute the minority of amplified fragments (less than 50 percent but often less than 20 percent), while the remainder are commonly referred to as constant AFLP fragments. The latter are nevertheless useful in the gel scoring procedure as they serve as anchor points to calculate fragments mobilities of AFLP markers and aid in quantifying the markers for co-dominant scoring. Co-dominant scoring (scoring for homo- or heterozygosity) of AFLP markers currently is restricted to the context of fingerprinting a segregating population. In a panel of unrelated lines, only dominant scoring is possible.

Although the throughput of AFLP is very high due to high multiplexing levels in the amplification and detection steps, the rate limiting step is the resolving power of electrophoresis. Electrophoresis allows unique identification of the majority of amplified fragments based on the combination of restriction enzyme combinations (EC), primer combinations (PC) and mobility, but ideally, the detection system should be capable of determining the entire sequence of the amplified fragments to capture all polymorphisms.

Detection by sequencing instead of mobility determination will increase throughput because:

1) polymorphisms located in the internal sequences will be detected in most (or all) amplified fragments; this will increase the number of markers per PC considerably.

2) no loss of AFLP markers due to co-migration of AFLP markers and constant bands.

3) co-dominant scoring does not rely on quantification of band intensities and is independent of the relatedness of the individuals fingerprinted.

So far, detection of AFLP markers/sequences by sequencing has not been economically feasible due to, among other limitations, cost limitations of Sanger dideoxy sequencing technology and other conventional sequencing technologies.

Accordingly, it is one of the goals of the present invention to provide for economically feasible methods for the detection of AFLP markers or other genetic markers such as SNP markers based on sequencing.

An important problem further associated with detection of a collection of AFLP or SNP containing fragments via sequencing for genotyping (i.e. diagnostic) purposes is that of sampling variation. Specifically, this means that when a collection of fragments is analyzed and particular fragments are not observed, one has to make sure that this is not due to the fact that the fragments involved were not sampled at the detection step, although they are present in the fragment mixture, because this would lead to false-negative scoring of the marker. This limitation does not apply to detection by electrophoresis because position information on the gel is available.

Accordingly, it is one of the further goals of the present invention provide a method that solves the problem of sample variation or at least reduces the errors caused by sample variation to an acceptable minimum.

SUMMARY OF THE INVENTION

The present inventors have found that sequencing is within reach for the detection of AFLP and SNP markers with the use of AFLP in certain adapted procedures for high throughput sequencing. The invention thus provides a method or strategy which combines the power and generic applicability of AFLP with certain high throughput sequencing technologies to establish a generically applicable polymorphism scoring system. In this strategy, the issue of sampling variation is also addressed to ensure genotyping with high accuracy and maximizing chances for datasets with minimal numbers of missing genotypes.

DEFINITIONS

In the following description and examples a number of terms are used. In order to provide a clear and consistent understanding of the specification and claims, including the scope to be given such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

Polymorphism: polymorphism refers to the presence of two or more variants of a nucleotide sequence in a population. A polymorphism may comprise one or more base changes, an insertion, a repeat, or a deletion. A polymorphism includes e.g. a simple sequence repeat (SSR) and a single nucleotide polymorphism (SNP), which is a variation, occurring when a single nucleotide: adenine (A), thymine (T), cytosine (C) or guanine (G)—is altered. A variation must generally occur in at least 1% of the population to be considered a SNP. SNPs make up e.g. 90% of all human genetic variations, and occur every 100 to 300 bases along the human genome. Two of every three SNPs substitute Cytosine (C) with Thymine (T). Variations in the DNA sequences of e.g. humans or plants can affect how they handle diseases, bacteria, viruses, chemicals, drugs, etc.

Nucleic acid: a nucleic acid according to the present invention may include any polymer or oligomer of pyrimidine and purine bases, preferably cytosine, thymine, and uracil, and adenine and guanine, respectively (See Albert L. Lehninger, *Principles of Biochemistry*, at 793-800 (Worth Pub. 1982) which is herein incorporated by reference in its entirety for all purposes). The present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogenous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

Complexity reduction: the term complexity reduction is used to denote a method wherein the complexity of a nucleic acid sample, such as genomic DNA, is reduced by the generation of a subset of the sample. This subset can be representative for the whole (i.e. complex) sample and is preferably a reproducible subset. Reproducible means in this context that when the same sample is reduced in complexity using the same method, the same, or at least comparable, subset is obtained. The method used for complexity reduction may be any method for complexity reduction known in the art. A preferred example of a method for complexity reduction includes for example AFLP® (Keygene N. V., the Netherlands; see e.g. EP 0 534 858, US6045994), the methods described by Dong (see e.g. WO 03/012118, WO 00/24939), indexed linking (Unrau et al., vide infra), linker-PCR (WO90/008821), and SALSA-PCR (WO00/23620) Schouten et al) etc. The complexity reduction methods used in the present invention have in common that they are reproducible. Reproducible in the sense that when the same sample is reduced in complexity in the same manner, the same subset of the sample is obtained, as opposed to more random complexity reduction such as microdissection or the use of mRNA (cDNA) which represents a portion of the genome transcribed in a selected tissue and for its reproducibility is depending on the selection of tissue, time of isolation etc.

AFLP: AFLP refers to a method for selective amplification of DNA based on digesting a nucleic acid with one or more restriction endonucleases to yield restriction fragments, ligating adaptors to the restriction fragments and amplifying the adaptor-ligated restriction fragments with at least one primer that is (part) complementary to the adaptor, (part) complementary to the remains of the restriction endonuclease, and that further contains at least one randomly selected nucleotide from amongst A, C, T, or G (or U as the case may be). AFLP does not require any prior sequence information and can be performed on any starting DNA. In general, AFLP comprises the steps of:
 (a) digesting a nucleic acid, in particular a DNA or cDNA, with one or more specific restriction endonucleases, to fragment the DNA into a corresponding series of restriction fragments;
 (b) ligating the restriction fragments thus obtained with a double-stranded synthetic oligonucleotide adaptor, one end of which is compatible with one or both of the ends of the restriction fragments, to thereby produce adapter-ligated, preferably tagged, restriction fragments of the starting DNA;
 (c) contacting the adapter-ligated, preferably tagged, restriction fragments under hybridizing conditions with one or more oligonucleotide primers that contain selective nucleotides at their 3'-end;
 (d) amplifying the adapter-ligated, preferably tagged, restriction fragment hybridised with the primers by PCR or a similar technique so as to cause further elongation of the hybridised primers along the restriction fragments of the starting DNA to which the primers hybridised; and
 (e) detecting, identifying or recovering the amplified or elongated DNA fragment thus obtained.

AFLP thus provides a reproducible subset of adaptor-ligated fragments. AFLP is described in EP 534858, U.S. Pat. No. 6,045,994 and in Vos et al. Reference is made to these publications for further details regarding AFLP. The AFLP is commonly used as a complexity reduction technique and a DNA fingerprinting technology. Within the context of the use of AFLP as a fingerprinting technology, the concept of an AFLP marker has been developed.

AFLP marker: An AFLP marker is an amplified adaptor-ligated restriction fragment that is different between two samples that have been amplified using AFLP (fingerprinted), using the same set of primers. As such, the presence or absence of this amplified adaptor-ligated restriction fragment can be used as a marker that is linked to a trait or phenotype. In conventional gel technology, an AFLP marker shows up as a band in the gel located at a certain mobility. Other electrophoretic techniques such as capillary electrophoresis may not refer to this as a band, but the concept remains the same, i.e.

a nucleic acid with a certain length and mobility. Absence or presence of the band may be indicative of (or associated with) the presence or absence of the phenotype. AFLP markers typically involve SNPs in the restriction site of the endonuclease or the selective nucleotides. Occasionally, AFLP markers may involve indels in the restriction fragment.

SNP marker: a SNP marker is a marker that is based on an identified single nucleotide polymorphism at a certain position. SNP markers can be located at identical positions to AFLP markers, but SNP markers can also be located in the restriction fragment itself. As such the genus SNP markers thus encompasses the species AFLP markers.

Constant band: a constant band in the AFLP technology is an amplified adaptor-ligated restriction fragment that is relatively invariable between samples. Thus, a constant band in the AFLP technology will, over a range of samples, show up at about the same position in the gel, i.e. has the same length/mobility. In conventional AFLP these are typically used to anchor the lanes corresponding to samples on a gel or electropherograms of multiple AFLP samples detected by capillary electrophoresis. Typically, a constant band is less informative than an AFLP marker. Nevertheless, as AFLP markers customary involve SNPs in the selective nucleotides or the restriction site, constant bands may comprise SNPs in the restriction fragments themselves, rendering the constant bands an interesting alternative source of genetic information that is complementary to AFLP markers.

Selective base: Located at the 3' end of the primer that contains a part that is complementary to the adaptor and a part that is complementary to the remains of the restriction site, the selective base is randomly selected from amongst A, C, T or G. By extending a primer with a selective base, the subsequent amplification will yield only a reproducible subset of the adaptor-ligated restriction fragments, i.e. only the fragments that can be amplified using the primer carrying the selective base. Selective nucleotides can be added to the 3' end of the primer in a number varying between 1 and 10. Typically 1-4 suffice. Both primers may contain a varying number of selective bases. With each added selective base, the subset reduces the amount of amplified adaptor-ligated restriction fragments in the subset by a factor of about 4. Typically, the number of selective bases used in AFLP is indicated by +N+M, wherein one primer carries N selective nucleotides and the other primers carries M selective nucleotides. Thus, an Eco/Mse +1/+2 AFLP is shorthand for the digestion of the starting DNA with EcoRI and MseI, ligation of appropriate adaptors and amplification with one primer directed to the EcoRI restricted position carrying one selective base and the other primer directed to the MseI restricted site carrying 2 selective nucleotides.

Clustering: with the term "clustering" is meant the comparison of two or more nucleotide sequences based on the presence of short or long stretches of identical or similar nucleotides. Several methods for alignment of nucleotide sequences are known in the art, as will be further explained below. Sometimes the terms "assembly" or "alignment" are used as synonyms.

Tag: a short sequence that can be added to a primer or included in its sequence or otherwise used as label to provide a unique identifier. Such a sequence identifier can be a unique base sequence of varying but defined length uniquely used for identifying a specific nucleic acid sample. For instance 4 bp tags allow 4(exp4)=256 different tags. Typical examples are ZIP sequences, known in the art as commonly used tags for unique detection by hybridization (Iannone et al. Cytometry 39:131-140, 2000). Using such a tag, the origin of a PCR sample can be determined upon further processing. In the case of combining processed products originating from different nucleic acid samples, the different nucleic acid samples are generally identified using different tags. In the case of the present invention, the addition of a unique sequence tag serves to identify the coordinates of the individual plant in the pool of sequences amplification products. Multiple tags can be used.

Tagging: the term tagging refers to the addition of a tag to a nucleic acid sample in order to be able to distinguish it from a second or further nucleic acid sample. Tagging can e.g. be performed by the addition of a sequence identifier during complexity reduction or by any other means known in the art. Such sequence identifier can e.g. be a unique base sequence of varying but defined length uniquely used for identifying a specific nucleic acid sample. Typical examples thereof are for instance ZIP sequences. Using such a tag, the origin of a sample can be determined upon further processing. In case of combining processed products originating from different nucleic acid samples, the different nucleic acid samples should be identified using different tags.

Tagged library: the term tagged library refers to a library of tagged nucleic acids.

Sequencing: The term sequencing refers to determining the order of nucleotides (base sequences) in a nucleic acid sample, e.g. DNA or RNA.

High-throughput screening: High-throughput screening, often abbreviated as HTS, is a method for scientific experimentation especially relevant to the fields of biology and chemistry. Through a combination of modern robotics and other specialised laboratory hardware, it allows a researcher to effectively screen large amounts of samples simultaneously.

Restriction endonuclease: a restriction endonuclease or restriction enzyme is an enzyme that recognizes a specific nucleotide sequence (target site) in a double-stranded DNA molecule, and will cleave both strands of the DNA molecule at every target site.

Restriction fragments: the DNA molecules produced by digestion with a restriction endonuclease are referred to as restriction fragments. Any given genome (or nucleic acid, regardless of its origin) will be digested by a particular restriction endonuclease into a discrete set of restriction fragments. The DNA fragments that result from restriction endonuclease cleavage can be further used in a variety of techniques and can for instance be detected by gel electrophoresis.

Gel electrophoresis: in order to detect restriction fragments, an analytical method for fractionating double-stranded DNA molecules on the basis of size can be required. The most commonly used technique for achieving such fractionation is (capillary) gel electrophoresis. The rate at which DNA fragments move in such gels depends on their molecular weight; thus, the distances travelled decrease as the fragment lengths increase. The DNA fragments fractionated by gel electrophoresis can be visualized directly by a staining procedure e.g. silver staining or staining using ethidium bromide, if the number of fragments included in the pattern is sufficiently small. Alternatively further treatment of the DNA fragments may incorporate detectable labels in the fragments, such as fluorophores or radioactive labels.

Ligation: the enzymatic reaction catalyzed by a ligase enzyme in which two double-stranded DNA molecules are covalently joined together is referred to as ligation. In general, both DNA strands are covalently joined together, but it is also possible to prevent the ligation of one of the two strands through chemical or enzymatic modification of one of the ends of the strands. In that case the covalent joining will occur in only one of the two DNA strands.

Synthetic oligonucleotide: single-stranded DNA molecules having preferably from about 10 to about 50 bases, which can be synthesized chemically are referred to as synthetic oligonucleotides. In general, these synthetic DNA molecules are designed to have a unique or desired nucleotide sequence, although it is possible to synthesize families of molecules having related sequences and which have different nucleotide compositions at specific positions within the nucleotide sequence. The term synthetic oligonucleotide will be used to refer to DNA molecules having a designed or desired nucleotide sequence.

Adaptors: short double-stranded DNA molecules with a limited number of base pairs, e.g. about 10 to about 30 base pairs in length, which are designed such that they can be ligated to the ends of restriction fragments. Adaptors are generally composed of two synthetic oligonucleotides which have nucleotide sequences which are partially complementary to each other. When mixing the two synthetic oligonucleotides in solution under appropriate conditions, they will anneal to each other forming a double-stranded structure. After annealing, one end of the adaptor molecule is designed such that it is compatible with the end of a restriction fragment and can be ligated thereto; the other end of the adaptor can be designed so that it cannot be ligated, but this need not be the case (double ligated adaptors).

Adaptor-ligated restriction fragments: restriction fragments that have been capped by adaptors.

Primers: in general, the term primers refer to DNA strands which can prime the synthesis of DNA. DNA polymerase cannot synthesize DNA de novo without primers: it can only extend an existing DNA strand in a reaction in which the complementary strand is used as a template to direct the order of nucleotides to be assembled. We will refer to the synthetic oligonucleotide molecules which are used in a polymerase chain reaction (PCR) as primers.

DNA amplification: the term DNA amplification will be typically used to denote the in vitro synthesis of double-stranded DNA molecules using PCR. It is noted that other amplification methods exist and they may be used in the present invention without departing from the gist.

Selective hybridisation: relates to hybridisation, under stringent hybridisation conditions, of a nucleic acid sequence to a specified nucleic acid target sequence to a detectably greater degree (e.g., at least 2-fold over background) than its hybridisation to non-target nucleic acid sequences and to the substantial exclusion of non-target nucleic acids. The terms "stringent conditions" or "stringent hybridisation conditions" includes reference to conditions under which a probe will hybridise to its target sequence, to a detectably greater degree than other sequences (e.g., at least 2-fold over background). Stringent conditions are sequence-dependent and will be different in different circumstances. By controlling the stringency of the hybridisation and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 100 nucleotides in length, optionally no more than 50, or 25 nucleotides in length. Typically, stringent conditions will be those in which the salt concentration is less than about 1.5 M Na ion, typically about 0.01 to 1.0 M Na ion concentration (or other salts) at pH 7.0 to 8.3 and the temperature is at least about is 30° C. for short probes (e.g., 10 to 50 nucleotides) and at least about 60° C. for long probes (e.g., greater than 50 nucleotides). Stringent conditions may also be achieved with the addition of destabilising agents such as formamide.

Exemplary low stringency conditions include hybridisation with a buffer solution of 30 to 35% formamide, 1 M NaCl, 1% SDS (sodium dodecylsulphate) at 37° C., and a wash in 1*to 2*SSC (20*SSC=3.0 M NaCl/0.3 M trisodium citrate) at 50 to 55° C. Exemplary moderate stringency conditions include hybridisation in 40 to 45% formamide, 1 M NaCl, 1% SDS at 37° C., and a wash in 0.5* to 1*SSC at 55 to 60° C. Exemplary high stringency conditions include hybridisation in 50% formamide, 1 M NaCl, 1% SDS at 37° C., and a wash in 0.1*SSC at 60 to 65° C. Specificity is typically the function of post-hybridisation washes, the critical factors being the ionic strength and temperature of the final wash solution. For DNA-DNA hybrids, the Tm can be approximated from the equation of Meinkoth and Wahl, Anal. Biochem., 138:267-284 (1984): Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridisation solution, and L is the length of the hybrid in base pairs. The Tm is the temperature (under defined ionic strength and pH) at which 50% of a complementary target sequence hybridises to a perfectly matched probe. Tm is reduced by about 1° C. for each 1% of mismatching; thus, Tm, hybridisation and/or wash conditions can be adjusted to hybridise to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilise a hybridisation and/or wash at 1, 2, 3, or 4° C. lower than the thermal melting point (Tm); moderately stringent conditions can utilise a hybridisation and/or wash at 6, 7, 8, 9, or 10° C. lower than the thermal melting point (Tm); low stringency conditions can utilise a hybridisation and/or wash at 11, 12, 13, 14, 15, or 20° C. lower than the thermal melting point (Tm). Using the equation, hybridisation and wash compositions, and desired Tm, those of ordinary skill will understand that variations in the stringency of hybridisation and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridisation of nucleic acids is found in Tijssen, Laboratory Techniques in Biochemistry and Molecular Biology-Hybridisation with Nucleic Acid Probes, Part 1, Chapter 2 "Overview of principles of hybridisation and the strategy of nucleic acid probe assays", Elsevier, N.Y. (1993); and Current Protocols in Molecular Biology, Chapter 2, Ausubel, et al., Eds., Greene Publishing and Wiley-Interscience, New York (1995).

DETAILED DESCRIPTION OF THE INVENTION

In a first aspect the present invention relates to a method for the high throughput discovery, detection and large-scale genotyping of one or more genetic markers in one or more samples, comprising the steps of:
(a) providing DNA from one or more samples;
(b) restricting the DNA with at least one restriction endonuclease to produce restriction fragments;
(c) ligating adaptors to the restriction fragments to produce adaptor-ligated restriction fragments;
(d) optionally, amplifying the adaptor-ligated restriction fragments with a primer pair that is at least complementary to the adaptors to produce pre-amplified adaptor-ligated restriction fragments;

(e) amplifying the (optionally pre-amplified) adaptor-ligated restriction fragments with a primer pair, wherein at least one of the primers contains an identifier tag at the 5' end of the primer to produce a library of tagged amplified subsets of adaptor-ligated restriction fragments for each sample;

(f) optionally, pooling the libraries derived from multiple samples;

(g) sequencing the libraries using high throughput sequencing technology;

(h) clustering the sequences per library, using the identifier tag;

(i) identify genetic markers by comparing clustered sequences within a library and/or between the libraries.

(j) determine (co-)dominant genotypes of the genetic markers in the one or more libraries, preferably for all samples and for all identified markers.

The method relates to the discovery, detection and genotyping of one or more genetic markers in one or more samples. In certain embodiments, the methods relates to presence/absence scoring of the genetic markers of interest. In certain embodiments the method relates to determination of (co-)dominant genotypes of one more samples for one or more genetic markers. This may require normalisation of the observed number of marker- or marker allele sequences between samples.

In the first step (a) of the method, DNA is to be provided. This can be done by methods known in the art per se. The isolation of DNA is generally achieved using common methods in the art such as the collection of tissue from a member of the population, DNA extraction (for instance using the Q-Biogene fast DNA kit), quantification and normalisation to obtain equal amounts of DNA per sample. The DNA can be from a variety of sources (Genomic, RNA, cDNA, BAc, YAC etc.) and organisms (human, mammal, plant, microorganisms, etc.). The isolated DNA may be pooled.

The DNA is restricted in step (b) using at least one restriction endonuclease. Depending on the case, i.e. size of genome, more endonucleases can be used. In certain embodiments, 2 or more endonucleases can be used. For most genomes 2 endonucleases are sufficient and this is hence most preferred. In certain embodiments, especially for large or complex genomes, more endonucleases can be used. Preferably the endonuclease provides for relatively short restriction fragments in the order of 250-500 bp, but this is not essential. Typically, at least one frequent cutting endonuclease is preferred, i.e. endonucleases that have a 4 or 5 base pair recognition sequence. One such enzyme is MseI, but numerous others are commercially available and can be used. Also enzymes that cut outside their recognition sequence can be used (Hs type), or enzymes that provide blunt ended restriction fragments. A preferred combination uses one rare (6 and more base pair recognition sequence, for example EcoRI) and one frequent cutter.

After restriction of the pooled DNAs, or simultaneously therewith, adaptors are ligated to the restriction fragments to provide for adaptor-ligated restriction fragments. One or more different adaptors may be used, for instance two adaptors, one forward, one reverse adaptor. Alternatively one adaptor may be used for all fragments or sets of adaptors may be used that at the overhanging end of the adaptor contain permutations of nucleotides such as to provide for indexing linkers that may allow for a pre-selection step (Unrau et al., Gene, 1994, 145, 163-169). Alternatively, blunt ended adaptors can be used, in the case of blunt ended restriction fragments. Adaptor-ligation is well known in the art and is described inter alia in EP 534858. One useful variant of the AFLP technology uses no selective nucleotides (i.c. +0/+0 primers) and is sometimes called linker PCR. As with Salsa PCR, the selection step is provided by the use of restriction enzymes, different restriction enzymes yields different subsets. This is sometimes also denoted as a pre-amplification wherein primers are used that are at least complementary to the adapters and optionally also to part of the remains of the recognition sequence of the restriction endonuclease. Pre-amplification may serve to (further) normalize the amount of DNA from each sample, or to increase the total amount of DNA to allow for multiple analysis (i.e. splitting up samples) and to enhance the signal-to-noise ratio. Pre-amplification may also be used to introduce tags that allow pooling prior to selective amplification. By the introduction of nucleotide tags (for instance 4 bp) at the 5' end of the primer, restriction fragments for a distinct sample can be tagged and at the end of the process can be retrieved by using the tag.

The adaptor-ligated restriction fragments are, after the optional pre-amplification, amplified in step (d) of the method of the invention with a pair of primers. One of the primers is complementary to at least part of the adaptor and may further be complementary to part of the remainder of the recognition sequence of the endonuclease and may further contain (randomly selected) selective nucleotides at its 3'-end, similar as is described in EP534858. Preferably the primers are capable of selectively hybridising under stringent hybridisation conditions. The selective amplification can also be performed with primers that carry a 5' tag to identify the origin of the sample, similar as above. The result is a library of (tagged) subsets of amplified adaptor-ligated restriction fragments.

The selectively amplified fragments in the libraries prepared from multiple samples can optionally be pooled at this point This may be useful in case markers are sought which are specific for certain groups of samples, such as those sharing certain phenotypic characteristics. Screening pooled samples is commonly referred to as bulked segregant analysis (BSA; Michelmore, Paran and Kesseli, 1991). In certain embodiments, pooling can also be performed before DNA extraction in the sampling stage, reducing the number of DNA preparations. Pooling of the DNA further serves to normalise the DNAs prior to PCR amplification to provide for a more equal representation in the libraries for sequencing.

The, optionally pooled, libraries of selectively amplified adaptor-ligated restriction fragments are now sequenced using high throughput sequencing technology.

The sequencing may in principle be conducted by any means known in the art, such as the dideoxy chain termination method (Sanger sequencing). It is however preferred and more advantageous that the sequencing is performed using high-throughput sequencing methods, such as the methods disclosed in WO 03/004690, WO 03/054142, WO 2004/069849, WO 2004/070005, WO 2004/070007, and WO 2005/003375 (all in the name of 454 Life Sciences), by Seo et al. (2004) Proc. Natl. Acad. Sci. USA 101:5488-93, and technologies of Helios, Solexa, US Genomics, etcetera, which are herein incorporated by reference. It is most preferred that sequencing is performed using the apparatus and/or method disclosed in WO 03/004690, WO 03/054142, WO 2004/069849, WO 2004/070005, WO 2004/070007, and WO 2005/003375 (all in the name of 454 Life Sciences), which are herein incorporated by reference. The technology described currently allows sequencing of up to 40 million bases in a single run and is 100 times faster and cheaper than competing technology based on Sanger sequencing and using currently available capillary electrophoresis instruments such as MegaBACE (GE Healthcare) or ABI3700(x1) (Applied Biosystems). This will increase with increasing read length per reaction and/or increasing numbers of parallel reactions. The sequencing technology roughly consists of 5 steps: 1) fragmentation of DNA and ligation of specific adaptor to create a library of single-stranded DNA (ssDNA); 2) annealing of ssDNA to beads, emulsification of the beads in water-in-oil microreactors and performing emulsion PCR to amplify the individual ssDNA molecules on beads; 3) selection of/enrichment for beads containing amplified ssDNA molecules on their surface 4) deposition of DNA carrying beads in a PicoTiterPlate®; and 5) simultaneous sequencing in 100,000 wells by generation of a pyrophosphate light signal.

In a preferred embodiment, the sequencing comprises the steps of:

(1) annealing sequencing-adaptor-ligated fragments to beads, each bead annealing with a single fragment;

(2) emulsifying the beads in water-in-oil micro reactors, each water-in-oil micro reactor comprising a single bead;

(3) performing emulsion PCR to amplify adaptor-ligated fragments on the surface of beads (4) selecting/enriching beads containing amplified adaptor-ligated fragments;

(5) loading the beads in wells, each well comprising a single bead; and (6) generating a pyrophosphate signal.

In the first step (1), the adaptors that are present in the adaptor ligated restriction fragments are annealed to the beads. As outlined herein before, the sequencing adaptor includes at least a "key" region for annealing to a bead, a sequencing primer region and a PCR primer region. In particular, the amplified adaptor-ligated restriction fragments now contain at one of the ends the following sequence 5'-Sequence primer binding site---Tag---PCR primer sequence-3', while at the other end a segment is present that may be as follows: 5'-Bead annealing sequence---Tag---Adaptor specific sequence---restriction site-specific sequence (optional)---(randomly) selective sequence (optional)-3'. It may be clear that the Sequence primer binding site and the Bead annealing sequence may be interchanged. This Bead annealing sequence can now be used for annealing the fragments to the bead, the bead carrying a nucleotide sequence to that end.

Thus, adapted fragments are annealed to beads, each bead annealing with a single adapted fragment. To the pool of adapted fragments, beads are added in excess as to ensure annealing of one single adapted fragment per bead for the majority of the beads (Poisson distribution).

In a preferred embodiment, to increase the efficiency of the screening further, it is beneficial to amplify the PCR product directionally onto the bead for sequencing. This can be accomplished to perform the PCR with adaptor-tailed PCR primers of which one strand of the adaptor on the MseI (or other restriction enzyme) side is complementary to the oligonucleotide coupled to the sequence beads.

In a next step, the beads are emulsified in water-in-oil microreactors, each water-in-oil microreactor comprising a single bead. PCR reagents are present in the water-in-oil microreactors allowing a PCR reaction to take place within the microreactors. Subsequently, the microreactors are broken, and the beads comprising DNA (DNA positive beads) are enriched.

In a following step, the beads are loaded in wells, each well comprising a single bead. The wells are preferably part of a PicoTiterTMPlate allowing for simultaneous sequencing of a large amount of fragments.

After addition of enzyme-carrying beads, the sequence of the fragments is determined using pyrosequencing. In successive steps, the PicoTiterTMPlate and the beads as well as the enzyme beads therein are subjected to different deoxyribonucleotides in the presence of conventional sequencing reagents, and upon incorporation of a deoxyribonucleotide a light signal is generated which is recorded. Incorporation of the correct nucleotide will generate a pyrosequencing signal which can be detected.

Pyrosequencing itself is known in the art and described inter alia on www.biotagebio.com; www.pyrosequencing.com/section technology. The technology is further applied in e.g. WO 03/004690, WO 03/054142, WO 2004/069849, WO 2004/070005, WO 2004/070007, and WO 2005/003375 (all in the name of 454 Life Sciences), which are herein incorporated by reference.

After sequencing, the sequences of the fragments that are directly obtained from the sequencing step may be trimmed, preferably in silico, to remove any bead annealing sequence, sequencing primer, adaptor or primer-related sequence information.

Typically, the alignment or clustering is performed on sequence data that have been trimmed for any added adaptors/primer sequences i.e. using only the sequence data from the fragments that originate from the nucleic acid sample, together with the optional identifier tag.

Methods of alignment of sequences for comparison purposes are well known in the art. Various programs and alignment algorithms are described in: Smith and Waterman (1981) Adv. Appl. Math. 2:482; Needleman and Wunsch (1970) J. Mol. Biol. 48:443; Pearson and Lipman (1988) Proc. Natl. Acad. Sci. USA 85:2444; Higgins and Sharp (1988) Gene 73:237-244; Higgins and Sharp (1989) CABIOS 5:151-153; Corpet et al. (1988) Nucl. Acids Res. 16:10881-90; Huang et al. (1992) Computer Appl. in the Biosci. 8:155-65; and Pearson et al. (1994) Meth. Mol. Biol. 24:307-31, which are herein incorporated by reference. Altschul et al. (1994) Nature Genet. 6:119-29 (herein incorporated by reference) present a detailed consideration of sequence alignment methods and homology calculations.

The NCBI Basic Local Alignment Search Tool (BLAST) (Altschul et al., 1990) is available from several sources, including the National Center for Biological Information (NCBI, Bethesda, Md.) and on the Internet, for use in connection with the sequence analysis programs blastp, blastn, blastx, tblastn and tblastx. It can be accessed at <http://www.ncbi.nlm.nih.gov/BLAST/>. A description of how to determine sequence identity using this program is available at <http://www.ncbi.nlm.nih.gov/BLAST/blast_help.html>. The database preferably comprises EST sequences, genomic sequences of the species of interest and/or the non-redundant sequence database of GenBank or similar sequence databases.

High throughput sequencing methods can be used as described in Shendure et al. Science, Vol 309, Issue 5741, 1728-1732. Examples thereof are microelectrophoretic sequencing, Hybridization sequencing/sequencing by hybridization (SBH), cyclic-array sequencing on amplified molecules, cyclic-array sequencing on single molecules, Non-cyclical, single-molecule, real-time methods, such as polymerase sequencing, exonuclease sequencing, nanopore sequencing.

Within the library the presence of a genetic marker and/or the genotype of the sample for a genetic marker can now be determined.

The method of the present invention can be used for the identification, detection of genotype determination AFLP markers, but also for the identification, detection and genotyping of SNP markers contained in constant bands.

To provide a solution to the problem of sampling variation which affects the accuracy of genotyping genetic markers by sequencing allelic (marker) fragments contained in a library of multiple fragments, the present inventors have also found that detection of AFLP markers via sequencing is preferably performed with sufficient redundancy (depth) to sample all amplified fragments at least once and accompanied by statistical means which address the issue of sampling variation in relation to the accuracy of the genotypes called. Furthermore, just as with AFLP scoring, in the context of a segregating population, the simultaneous scoring of the parent individuals in one experiment, will aid in determining the statistical threshold, because all possible alleles in the sample will be scored in either parent 1 or parent 2. Note that it is suggested to sample parent individuals with higher redundancy than individuals of segregating populations.

Thus, in certain embodiments, the redundancy of the tagged amplified adaptor-ligated restriction fragments is at least 6, preferably at least 7, more preferably at least 8 and most preferably at least 9. In certain embodiments, the sequence of each adaptor-ligated restriction fragment is determined at least 6, preferably at least 7, more preferably at least 8 and most preferably at least 9 fold. In certain embodiments, the redundancy is selected such, assuming a 50/50 overall chance of identifying the locus correctly as homozygous, that the chance of correct identification of the locus is more than 95%, 96%, 97%, 98%, 99%, 99.5%.

In certain embodiments, the number of samples can be varied between 1 and 100.000, this also largely depends on the size of the genome to be analysed and the number of selectively amplified fragments. Usually, the capacity of the sequencing technology employed provides the most limiting factor in this respect.

BRIEF DESCRIPTION OF THE DRAWINGS

FIGS. 2A and 2B show DNA concentration estimation using 2% agarose gel-electrophoresis. 51 denotes PSP11; S2 denote PI201234. 50, 100, 250 and 500 ng denotes respectively 50 ng, 100 ng, 250 ng and 500 ng to estimate DNA amounts of S1 and S2. FIGS. 2C and 2D show DNA concentration determination using Nanodrop spectrophotometry.

FIG. 4A shows flow charts of the sequence data processing pipeline, i.e. the steps taken from the generation of the sequencing data to the identification of putative SNPs, SSRs and indels, via steps of the removal of known sequence information in Trimming & Tagging resulting in trimmed sequence data which are clustered and assembled to yield contigs and singletons (fragments that cannot be assembled in a contig) after which putative polymorphisms can be identified and assessed. FIG. 4B further elaborates on the process of polymorphisms mining.

(SEQ ID NO: 38)
TAACACGACTTTGAACAAACCCAAACTCCCCCAATCGATTTCAAACCTAG
AACA[A/G]TGTTGGTTTTGGTGCTAACTTCAACCCCACTACTGTTTTGC
TCTATTTTTG.

Figure 6:
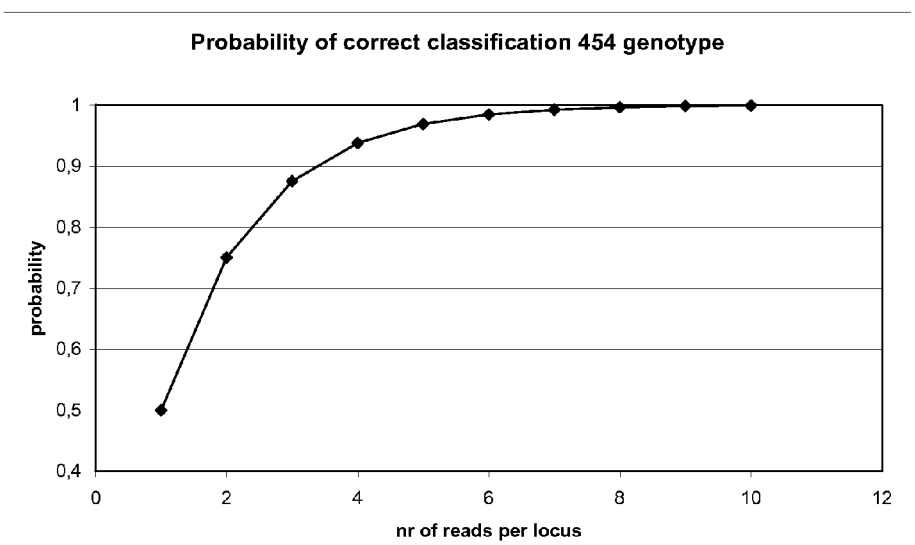

FIG. 6: Graphic representation of the probability of correct classification of the genotype based on the number of observed reads per locus.

EXAMPLES

The method is exemplified as follows:

1) AFLP templates are prepared according to a modified protocol of Vos et al. which involves a heat-denaturation step for 20 min at 80° C. between the restriction and ligation steps. After incubation for 20 min at 80° C., the restriction enzyme digest is cooled to room temperature and DNA ligase is added. The denaturation step leads to dissociation of the complementary strands of restriction fragments up to 120 bp such that no adaptors will be ligated to the ends. As a result, fragments smaller than 120 bp will not be amplified, hence size selection is achieved.

2) Pre-amplification reactions, if applicable, are performed as in conventional AFLP.

3) The last (selective) amplification step is performed using AFLP primers with unique identifier tags for every sample in the population/experiment, (using a unique 4 bp identifier sequence; KIS). The KIS are located at the 5' end of the selective AFLP primers. One additional selective nucleotide will be used in comparison with the number of selective bases used in conventional AFLP detection by electrophoresis, e.g. +4/+3 for an EcoRI/MseI fingerprint in pepper (gel detection +3/+3) and +4/+4 for and EcoRI/MseI fingerprint in maize (gel detection +4/+3). The number of selective nucleotides that are applied needs to be determined empirically; it may be so that the same number of selective nucleotides can be applied as used for gel detection. This number further depends on the number of samples included in the experiment, since the numbers of sequence traces is assumed to be fixed 200,000 at the current status of sequencing technology, but this may and probably will increase. Preferred starting point is to achieve 10-fold sampling of AFLP fragments per sample library.

4) The collection of samples prepared according to steps 1-4 is subjected to sequencing via 454 Life Sciences technology. This means that individual AFLP fragments are cloned on beads, PCR amplified and sequenced. An output of 200,000 sequences of 100 bp length is expected. For a collection of 100 samples, this equals an average of 2000 sequences traces/sample, traceable to sample nr. via the 5' tag.

5) Assuming the amplification of 100 AFLP fragments per PC when 1 additional selective nucleotide is used compared to the number used with gel detection, of which 90 percent are constant bands, the AFLP fragments are sampled with 20-fold average redundancy per fragment. However, since sequencing is non directional and most bands are >200 bp, sequencing redundancy will be slightly over 10-fold for each fragment end.

6) All sequences are clustered per sample using the KRS tag. Given a 10-fold over sampling, this means that 200 different sequence traces are expected per sample, representing 200×100 bp=20 kb sequence/sample. When 10 percent of these sequences are derived from AFLP markers (i.e. 1 allele is amplified and the other is absent in the PCR reaction), 90 percent (18 kb) of the sequences are derived from constant bands.

7) Two types of genetic markers are scored:

A) AFLP markers: these are sequences which are observed in some samples, but absent in others.

Inspection of the frequency of sequences in the collection of samples will reveal this category. Dominant scoring is performed depending on the presence/absence observation of these sequences in every sample. Reliable scoring of AFLP markers requires a statistical threshold to be set regarding the frequency with which other AFLP sequences are observed in the experiment. I.e. an AFLP marker can be scored as present (dominant) if the AFLP marker sequence is observed in the sample, but the reliability of the absent score depends on the (average) frequency of (constant) AFLP fragments. Statistical threshold levels are required such that presence/absence scoring is performed with preferably at least 99.5% accuracy, depending on the acceptable level needed for the specific application. If a segregating population and its parents is analysed, these markers can possibly be scored co-dominantly as well by defining frequency categories of the marker sequences. The latter may actually be complicated by the influence of sampling variation of the AFLP marker which differs between samples.

B) (SN) Polymorphisms in Constant AFLP Fragments.

This is the most interesting (and abundant) category of genetic markers. The essence is that SNP markers contained in the internal sequences of constant AFLP fragments are scored as co-dominant SNP markers. Again, this preferably requires applying a statistical threshold level for accurate calling of the presence or absence of an allele. A 10-fold sequencing redundancy of the fragment library is expected to be sufficient but a statistical analysis method is needed to determine accuracy of the SNP marker genotypes depending on the number each allele sequence is observed. The rationale is that when a constant band contains a SNP and one allele is observed e.g. 5 times while (the sequence containing the) other allele is not observed, it is highly likely that the sample is homozygous for the observed allele. Consequently, when both alleles are observed, the sample is scored heterozygous for the SNP marker, irrespective of their frequencies.

8) The result will be a genotyping table containing the genotypes of (co-)dominantly scored AFLP markers and co-dominantly scored SNPs, along with probabilities for correctness of the genotypes for all markers. Alternatively, a dataset is generated which contains genotypes which have surpassed the set statistical threshold level.

The approach assumes 10-fold over sampling of AFLP fragments per sample, yielding 18 kb of constant sequence/sample and 2 kb of AFLP marker sequences.

The numbers of genetic markers observed depends on the SNP rate in the germplasm investigated. Below, estimates of the numbers of genetic markers are provided at different germplasm SNP rates, when sampling 20 kb sequence. The average length of AFLP markers/fragments is assumed to be 200 bp:

TABLE 1

Expected numbers of genetic markers scored by sequencing AFLP fragments using 454 Life sciences technology assuming 10-fold over sampling, 200,000 sequence traces, 90 percent constant bands/10 percent AFLP markers at various SNP rates.

| SNP rate | AFLP markers (2 kb) | SNPs in constant bands (18 kb)* |
|---|---|---|
| 1/250 bp | 8 | 72 |
| 1/1000 bp | 2 | 18 |
| 1/2000 bp | 1 | 9 |
| 1/5000 bp | 0.4 | 3.6 |

*As the AFLP fragments may be sequenced from both ends, a proportion of the observed SNP can be derived from the same loci.

It is important to note that the numbers provided in table 1 are averages, which may differ between combinations of different primers. Analogous to conventional AFLP typing, identification of top primer combinations (PC) may yield higher numbers of markers per PC. In addition, the numbers presented in Table 1 may change depending on the required level of over sampling needed in order to reach the required accuracy level.

The calculation of the correct classification of the genotype is as follows:

$$P(\text{correct}) = P(aa) + P(AA) + P(Aa)^*[1 - 0.5^* \exp(n-1)]$$

Wherein P(aa) is the fraction of the population with genotype aa (in the enclosed graph, FIG. 9, set at 0.25. P(AA) is the fraction of the population with genotype AA (set at 0.25. P(Aa) is the fraction of the population with genotype Aa (in FIG. 6 and table below, set at 0.5. n equals the number of individuals.

TABLE

| n | P |
|---|---|
| 1 | 0.5 |
| 2 | 0.75 |
| 3 | 0.875 |
| 4 | 0.9375 |
| 5 | 0.96875 |
| 6 | 0.984375 |
| 7 | 0.992188 |
| 8 | 0.996094 |
| 9 | 0.998047 |
| 10 | 0.999023 |

Example 1

Pepper

DNA from the Pepper lines PSP-11 and PI201234 was used to generate AFLP product by use of AFLP Keygene Recognition Site specific primers. (These AFLP primers are essentially the same as conventional AFLP primers, e.g. described in EP 0 534 858, and will generally contain a recognition site region, a constant region and one or more selective nucleotides in a selective region.

From the pepper lines PSP-11 or PI201234 150 ng of DNA was digested with the restriction endonucleases EcoRI (5 U/reaction) and MseI (2 U/reaction) for 1 hour at 37° C.

following by inactivation for 10 minutes at 80° C. The obtained restriction fragments were ligated with double-stranded synthetic oligonucleotide adapter, one end of which is compatible with one or both of the ends of the EcoRI and/or MseI restriction fragments. The restriction ligation mixture was 10 times diluted and 5 microliter of each sample was pre-amplified (2) with EcoRI +1(A) and MseI +1(C) primers (set I). After amplification the quality of the pre-amplification product of the two pepper samples was checked on a 1% agarose gel. The preamplification products were 20 times diluted, followed by a KRSEcoRI +1(A) and KRSMseI +2(CA) AFLP pre-amplification. The KRS (identifier) sections are underlined and the selective nucleotides are in bold at the 3'-end in the primersequence SEQ ID 1-4 below. After amplification the quality of the pre-amplification product of the two pepper samples was checked on a 1% agarose gel and by an EcoRI +3(A) and MseI +3(C) (3) AFLP fingerprint (4). The pre-amplification products of the two pepper lines were separately purified on a QiagenPCR column (5). The concentration of the samples was measured on a NanoDrop® ND-1000 Spectrophotometer. A total of 5 micrograms PSP-11 and 5 micrograms PI201234 PCR products were mixed and sequenced.

Primer set I used for preamplification of PSP-11

E01LKRS1
[SEQ ID 1]
5'-CGTCAGACTGCGTACCAATTCA-'

M15KKRS1
[SEQ ID 2]
5'-TGGTGATGAGTCCTGAGTAACA-'

Primer set II used for preamplification of PI201234

E01LKRS2
[SEQ ID 3]
5'-CAAGAGACTGCGTACCAATTCA-3'

M15KKRS2
[SEQ ID 4]
5'-AGCCGATGAGTCCTGAGTAACA-3'

(1) EcoRI/MseI Restriction Ligation Mixture
Restriction Mix (40 ul/Sample)

| DNA | 6 μl (±300 ng) |
|---|---|
| ECoRI (5U) | 0.1 μl |
| MseI (2U) | 0.05 μl |
| 5xRL | 8 μl |
| MQ | 25.85 μl |
| Totaal | 40 μl |

Incubation during 1 h. at 37° C.
Addition of:
Ligation Mix (10 μl/Sample)

| 10 mM ATP | 1 μl |
|---|---|
| T4 DNA ligase | 1 μl |
| ECoRI adapt. (5 pmol/μl) | 1 μl |
| MseI adapt. . (50 pmol/μl) | 1 μl |
| 5xRL | 2 μl |
| MQ | 4 μl |
| Totaal | 10 μl |

Incubation during 3 h. at 37° C.

EcoRI-Adaptor

91M35/91M36:
[SEQ ID 5]
*-CTCGTAGACTGCGTACC:91M35

± bio
[SEQ ID 6]
CATCTGACGCATGGTTAA:91M36

MseI-Adaptor

92A18/92A19:
[SEQ ID 7]
5-GACGATGAGTCCTGAG-3:92A18

[SEQ ID 8]
3-TACTCAGGACTCAT-5:92A19

(2) Pre-Amplification
Preamplification (A/C):

| RL-mix (10x) | 5 μl |
|---|---|
| EcoRI-pr E01L(50 ng/ul) | 0.6 μl |
| MseI-pr M02K (50 ng/ul) | 0.6 μl |
| dNTPs (25 mM) | 0.16 μl |
| Taq.pol.(5U) | 0.08 μl |
| 10XPCR | 2.0 μl |
| MQ | 11.56 μl |
| Total | 20 μl/reaction |

Pre-Amplification Thermal Profile

Selective pre amplification was done in a reaction volume of 50 μl. The PCR was performed in a PE GeneAmp PCR System 9700 and a 20 cycle profile was started with a 94° C. denaturation step for 30 seconds, followed by an annealing step of 56° C. for 60 seconds and an extension step of 72° C. for 60 seconds.

EcoRI + 1(A)[1]
E01 L
[SEQ ID 9]
92R11:5-AGACTGCGTACCAATTCA-3

MseI + 1(C)[1]
M02k
[SEQ ID 10]
93E42:5-GATGAGTCCTGAGTAAC-3

Preamplification A/CA:

PA+1/+1-mix (20×): 5 μl

EcoRI-pr: 1.5 μl

MseI-pr.: 1.5 μl dNTPs (25 mM): 0.4 μl

Taq.pol. (5 U): 0.2 μl

10XPCR: 5 μl

MQ: 36.3 μl

Total: 50 μl

Selective pre amplification was done in a reaction volume of 50 μl. The PCR was performed in a PE GeneAmp PCR System 9700 and a 30 cycle profile was started with a 94° C. denaturation step for 30 seconds, followed by an annealing step of 56° C. for 60 seconds and an extension step of 72° C. for 60 seconds.

(3) KRSEcoRI +1(A) and KRSMseI +2(CA)$^2$

```
05F212
E01LKRS1
                                      [SEQ ID 11]
CGTCAGACTGCGTACCAATTCA-3'

05F213
E01LKRS2
                                      [SEQ ID 12]
CAAGAGACTGCGTACCAATTCA-3'

05F214
M15KKRS1
                                      [SEQ ID 13]
TGGTGATGAGTCCTGAGTAACA-3'

05F215
M15KKRS2
                                      [SEQ ID 14]
AGCCGATGAGTCCTGAGTAACA-3'
``` selective nucleotides in bold and tags (KRS) underlined
Sample PSP11: E01LKRS1/M15KKRS1
Sample PI120234: E01LKRS2/M15KKRS2

(4) AFLP Protocol

Selective amplification was done in a reaction volume of 20 µl. The PCR was performed in a PE GeneAmp PCR System 9700. A 13 cycle profile was started with a 94° C. denaturation step for 30 seconds, followed by an annealing step of 65° C. for 30 seconds, with a touchdown phase in which the annealing temperature was lowered 0.7° C. in each cycle, and an extension step of 72° C. for 60 seconds. This profile was followed by a 23 cycle profile with a 94° C. denaturation step for 30 seconds, followed by an annealing step of 56° C. for 30 seconds and an extension step of 72° C. for 60 seconds.

```
EcoRI + 3(AAC) and MseI + 3(CAG)
E32
                                      [SEQ ID 15]
92S02:  5-GACTGCGTACCAATTCAAC-3

M49
                                      [SEQ ID 16]
92G23:  5-GATGAGTCCTGAGTAACAG-3
```

(5) Qiagen Column

The AFLP product was purified by using the QIAquick PCR Purification Kit (QIAGEN) following the QIAquick® Spin Handbook 07/2002 page 18 and the concentration was measured with a NanoDrop® ND-1000 Spectrophotometer. A total of 5 µg of +1/+2 PSP-11 AFLP product and 5 µg of +1/+2 PI201234 AFLP product was put together and solved in 23.3 µl TE. Finally a mixture with a concentration of 430 ng/µl +1/+2 AFLP product was obtained.

Sequence Library Preparation and High-Throughput Sequencing

Figure 1A:
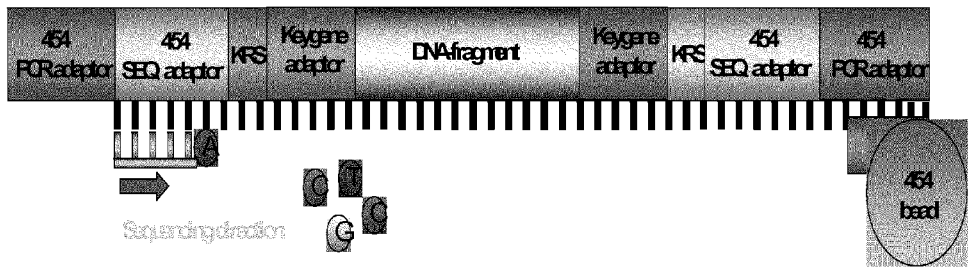
FIG. 1A shows a fragment according to the present invention annealed onto a bead ('454 bead') and the sequence of primer used for pre-amplification of the two pepper lines. 'DNA fragment' denotes the fragment obtained after digestion with a restriction endonuclease, 'keygene adaptor' denotes an adaptor providing an annealing site for the (phosphorylated) oligonucleotide primers (SEQ ID NOS 1-4, respectively, in order of appearance) used to generate a library, 'KRS' denotes an identifier sequence (tag), '454 SEQ. Adaptor' denotes a sequencing adaptor, and '454 PCR adaptor' denotes an adaptor to allow for emulsion amplification of the DNA fragment. The PCR adaptor allows for annealing to the bead and for amplification and may contain a 3'-T overhang.
Figure 1B:
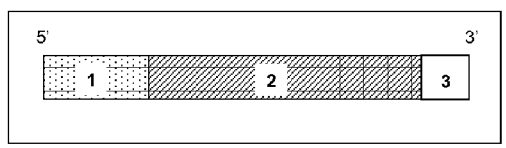
FIG. 1B shows a schematic primer used in the complexity reduction step. Such a primer generally comprises a recognition site region indicated as (2), a constant region that may include a tag section indicated as (1) and one or more selective nucleotides in a selective region indicated as (3) at the 3'-end thereof).

Mixed amplification products from both pepper lines were subjected to high-throughput sequencing using 454 Life Sciences sequencing technology as described by Margulies et al., (Margulies et al., Nature 437, pp. 376-380 and Online Supplements). Specifically, the AFLP PCR products were first end-polished and subsequently ligated to adaptors to facilitate emulsion-PCR amplification and subsequent fragment sequencing as described by Margulies and co-workers. 454 adaptor sequences, emulsion PCR primers, sequence-primers and sequence run conditions were all as described by Margulies and co-workers. The linear order of functional elements in an emulsion-PCR fragment amplified on Sepharose beads in the 454 sequencing process was as follows as exemplified in FIG. 1A:

454 PCR adaptor—454 sequence adaptor—4 bp AFLP primer tag 1—AFLP primer sequence 1 including selective nucleotide(s)—AFLP fragment internal sequence—AFLP primer sequence 2 including selective nucleotide(s), 4 bp AFLP primers tag 2-454 sequence adaptor—454 PCR adaptor—Sepharose bead Two high-throughput 454 sequence runs were performed by 454 Life Sciences (Branford, Conn.; United States of America).

454 Sequence Run Data-Processing.

Sequence data resulting from one 454 sequence run were processed using a bio-informatics pipeline (Keygene N.V.). Specifically, raw 454 basecalled sequence reads were converted in FASTA format and inspected for the presence of tagged AFLP adaptor sequences using a BLAST algorithm. Upon high-confidence matches to the known tagged AFLP primer sequences, sequences were trimmed, restriction endonuclease sites restored and assigned the appropriate tags (sample 1 EcoRI (ES1), sample 1 MseI (MS1), sample 2 EcoRI (ES2) or sample 2 MseI (MS2), respectively). Next, all trimmed sequences larger than 33 bases were clustered using a megaBLAST procedure based on overall sequence homologies. Next, clusters were assembled into one or more contigs and/or singletons per cluster, using a CAP3 multiple alignment algorithm. Contigs containing more than one sequence were inspected for the sequence mismatches, representing putative polymorphisms. Sequence mismatches were assigned quality scores based on the following criteria:

the numbers of reads in a contig the observed allele distribution

The above two criteria form the basis for the so called Q score assigned to each putative SNP/indel. Q scores range from 0 to 1; a Q score of 0.3 can only be reached in case both alleles are observed at least twice.

location in homopolymers of a certain length (adjustable; default setting to avoid polymorphism located in homopolymers of 3 bases or longer).

number of contigs in cluster.

distance to nearest neighboring sequence mismatches (adjustable; important for certain types of genotyping assays probing flanking sequences)

the level of association of observed alleles with sample 1 or sample 2; in case of a consistent, perfect association between the alleles of a putative polymorphism and samples 1 and 2, the polymorphism (SNP) is indicated as an "elite" putative polymorphism (SNP). An elite polymorphism is thought to have a high probability of being located in a unique or low-copy genome sequence in case two homozygous lines have been used in the discovery process. Conversely, a weak association of a polymorphism with sample origin bears a high risk of having discovered false polymorphisms arising from alignment of non-allelic sequences in a contig.

Sequences containing SSR motifs were identified using the MISA search tool (MIcroSAtellite identification tool; available from http://pgrc.ipk-gatersleben.de/misa/

Overall statistics of the run is shown in the Table below.

TABLE

Overall statistics of a 454 sequence run for SNP discovery in pepper.

| Enzyme combination | Run |
|---|---|
| Trimming | |
| All reads | 254308 |
| Fault | 5293 (2%) |
| Correct | 249015 (98%) |
| Concatamers | 2156 (8.5%) |
| Mixed tags | 1120 (0.4%) |

TABLE-continued

Overall statistics of a 454 sequence run for SNP discovery in pepper.

| Enzyme combination | Run |
|---|---|
| Correct reads | |
| Trimmed one end | 240817 (97%) |
| Trimmed both ends | 8198 (3%) |
| Number of reads sample 1 | 136990 (55%) |
| Number of reads sample 2 | 112025 (45 %) |
| Clustering | |
| Number of contigs | 21918 |
| Reads in contigs | 190861 |
| Average number reads per contig | 8.7 |
| SNP mining | |
| SNPs with Q score ≥ 0.3 * | 1483 |
| Indel with Q score ≥ 0.3 * | 3300 |
| SSR mining | |
| Total number of SSR motifs identified | 359 |
| Number of reads containing one or more SSR motifs | 353 |
| Number of SSR motif with unit size 1 (homopolymer) | 0 |
| Number of SSR motif with unit size 2 | 102 |
| Number of SSR motif with unit size 3 | 240 |
| Number of SSR motif with unit size 4 | 17 |

Figure 5:
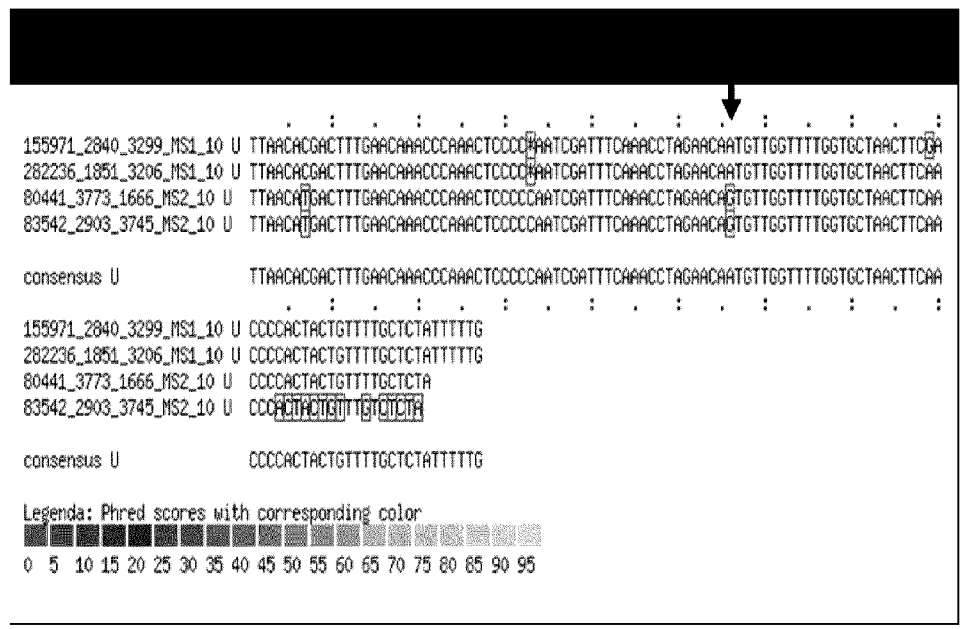
FIG. 5: Multiple alignment "10037_CL989contig2" of pepper AFLP fragment sequences (SEQ ID NOS 39-43, respectively, in order of appearance), containing a putative single nucleotide polymorphism (SNP). Note that the SNP (indicated by an the black arrow) is defined by an A allele present in both reads of sample 1 (PSP11), denoted by the presence of the MS1 tag in the name of the top two reads, and a G allele present in sample 2 (PI201234), denoted by the presence of the MS2 tag in the name of the bottom two reads. Read names are shown on the left. The consensus sequence of this multiple alignment is (5'-3')

SNP/indel mining criteria were as follows:

No neighbouring polymorphisms with Q score larger than 0.1 within 12 bases on either side, not present in homopolymers of 3 or more bases. Mining criteria did not take into account consistent association with sample 1 and 2, i.e. the SNPs and indels are not necessarily elite putative SNPs/indels An example of a multiple alignment containing an elite putative single nucleotide polymorphism is shown in FIG. 5.

Example 2

Maize

DNA from the Maize lines B73 and M017 was used to generate AFLP product by use of AFLP Keygene Recognition Site specific primers. (These AFLP primers are essentially the same as conventional AFLP primers, e.g. described in EP 0 534 858, and will generally contain a recognition site region, a constant region and one or more selective nucleotides at the 3'-end thereof).

DNA from the pepper lines B73 or M017 was digested with the restriction endonucleases TaqI (5 U/reaction) for 1 hour at 65° C. and MseI (2 U/reaction) for 1 hour at 37° C. following by inactivation for 10 minutes at 80° C. The obtained restriction fragments were ligated with double-stranded synthetic oligonucleotide adapter, one end of which is compatible with one or both of the ends of the TaqI and/or MseI restriction fragments.

AFLP preamplification reactions (20 μl/reaction) with +1/+1 AFLP primers were performed on 10 times diluted restriction-ligation mixture. PCR profile:20*(30 s at 94° C.+60 s at 56° C.+120 s at 72° C.). Additional AFLP reactions (50 μl/reaction) with different +2 TaqI and MseI AFLP Keygene Recognition Site primers (Table below, tags are in bold, selective nucleotides are underlined.) were performed on 20 times diluted +1/+1 TaqI/MseI AFLP preamplification product. PCR profile: 30*(30 s at 94° C.+60 s at 56° C.+120 s at 72° C.). The AFLP product was purified by using the QIAquick PCR Purification Kit (QIAGEN) following the QIAquick® Spin Handbook 07/2002 page 18 and the concentration was measured with a NanoDrop® ND-1000 Spectrophotometer. A total of 1.25 μg of each different B73 +2/+2 AFLP product and 1.25 μg of each different M017 +2/+2 AFLP product was put together and solved in 30 μl TE. Finally a mixture with a concentration of 333 ng/μl +2/+2 AFLP product was obtained.

TABLE

| SEQ ID | PCR Primer | Primer sequence | Maize | AFLP Reaction |
|---|---|---|---|---|
| [SEQ ID 17] | 05G360 | ACGTGTAGACTGCGTA CCGA<u>AA</u> | B73 | 1 |
| [SEQ ID 18] | 05G368 | ACGTGATGAGTCCTGA GTAA<u>CA</u> | B73 | 1 |
| [SEQ ID 19] | 05G362 | CGTAGTAGACTGCGTA CCGA<u>AC</u> | B73 | 2 |
| [SEQ ID 20] | 05G370 | CGTAGATGAGTCCTGA GTAA<u>CA</u> | B73 | 2 |
| [SEQ ID 21] | 05G364 | GTACGTAGACTGCGTA CCGA<u>AG</u> | B73 | 3 |
| [SEQ ID 22] | 05G372 | GTACGATGAGTCCTGA GTAA<u>CA</u> | B73 | 3 |
| [SEQ ID 23] | 05G366 | TACGGTAGACTGCGTA CCGA<u>AT</u> | B73 | 4 |
| [SEQ ID 24] | 05G374 | TACGGATGAGTCCTGA GTAA<u>CA</u> | B73 | 4 |
| [SEQ ID 25] | 05G361 | AGTCGTAGACTGCGTA CCGA<u>AA</u> | M017 | 5 |
| [SEQ ID 26] | 05G369 | AGTCGATGAGTCCTGA GTAA<u>CA</u> | M017 | 5 |
| [SEQ ID 27] | 05G363 | CATGGTAGACTGCGTA CCGA<u>AC</u> | M017 | 6 |
| [SEQ ID 28] | 05G371 | CATGGATGAGTCCTGA GTAA<u>CA</u> | M017 | 6 |
| [SEQ ID 29] | 05G365 | GAGCGTAGACTGCGTA CCGA<u>AG</u> | M017 | 7 |
| [SEQ ID 30] | 05G373 | GAGCGATGAGTCCTGA GTAA<u>CA</u> | M017 | 7 |
| [SEQ ID 31] | 05G367 | TGATGTAGACTGCGTA CCGA<u>AT</u> | M017 | 8 |
| [SEQ ID 32] | 05G375 | TGATGATGAGTCCTGA GTAA<u>CA</u> | M017 | 8 |

Figure 3:
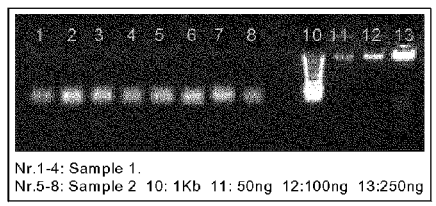
FIGS. 3A and 3B show the results of intermediate quality assessments of example 3.
FIG. 3C shows DNA concentrations of each sample noted using Nanodrop.
Figure 3C:
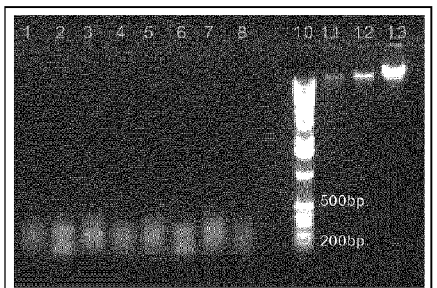

Finally the 4 P1-samples and the 4 P2-samples were pooled and concentrated. A total amount of 25 μl of DNA product and a final concentration of 400 ng/ul (total of 10 μg) was obtained. Intermediate quality assessments are given in FIG. 3.

Sequencing by 454

Pepper and maize AFLP fragment samples as prepared as described hereinbefore were processed by 454 Life Sciences as described (Margulies et al., 2005. Genome sequencing in microfabricated high-density picoliter reactors. Nature 437 (7057):376-80. Epub Jul. 31, 2005).

Data Processing

Processing Pipeline:

Input Data raw sequence data were received for each run:
  200,000-400,000 reads
  base calling quality scores Trimming and Tagging These sequence data are analyzed for the presence of Keygene Recognition Sites (KRS) at the beginning and end of the read. These KRS sequences consist of both AFLP-adaptor and sample label sequence and are specific for a certain AFLP primer combination on a certain sample. The KRS sequences are identified by BLAST and trimmed and the restriction sites are restored. Reads are marked with a tag for identification of the KRS origin. Trimmed sequences are selected on length (minimum of 33 nt) to participate in further processing.

Clustering and Assembly

A MegaBlast analysis is performed on all size-selected, trimmed reads to obtain clusters of homologous sequences. Consecutively all clusters are assembled with CAPS to result in assembled contigs. From both steps unique sequence reads are identified that do not match any other reads. These reads are marked as singletons.

The processing pipeline carrying out the steps described herein before is shown in FIG. 4A Polymorphism Mining and Quality Assessment The resulting contigs from the assembly analysis form the basis of polymorphism detection. Each 'mismatch' in the alignment of each cluster is a potential polymorphism. Selection criteria are defined to obtain a quality score:

- number of reads per contig
- frequency of 'alleles' per sample
- occurrence of homopolymer sequence
- occurrence of neighbouring polymorphisms SNPs and indels with a quality score above the threshold are identified as putative polymorphisms. For SSR mining we use the MISA (MIcroSAtellite identification) tool (http://pgrc.ipk-gatersleben.de/misa). This tool identifies di-, tri-, tetra-nucleotide and compound SSR motifs with predefined criteria and summarizes occurrences of these SSRs. The polymorphism mining and quality assignment process is shown in FIG. 4B Results The table below summarizes the results of the combined analysis of sequences obtained from 2 454 sequence runs for the combined pepper samples and 2 runs for the combined maize samples.

|  | Pepper | Maize |
|---|---|---|
| Total number of reads | 457178 | 492145 |
| Number of trimmed reads | 399623 | 411008 |
| Number singletons | 105253 | 313280 |
| Number of contigs | 31863 | 14588 |
| Number of reads in contigs | 294370 | 97728 |
| Total number of sequences containing SSRs | 611 | 202 |
| Number of different SSR-containing sequences | 104 | 65 |
| Number of different SSR motifs (di, tri, tetra and compound) | 49 | 40 |
| Number SNPs with Q score ≥ 0.3 * | 1636 | 782 |
| Number of indels * | 4090 | 943 |

* both with selection against neighboring SNPs, at least 12 bp flanking sequence and not occurring in homopolymer sequences larger than 3 nucleotides.

Example 3

SNP Validation by PCR Amplification and Sanger Sequencing

In order to validate the putative A/G SNP identified in example 1, a sequence tagged site (STS) assay for this SNP was designed using flanking PCR primers. PCR primer sequences were as follows:

Primer_1.2f:
[SEQ ID 33]
5'-AAACCCAAACTCCCCCAATC-3',
and

Primer_1.2r:
[SEQ ID 34]
5'-<u>AGCGGATAACAATTTCACACAGGACATCAGTAGTCACACTGGTACAA</u>

AAATAGAGCAAAACAGTAGTG-3'

Note that primer 1.2r contained an M13 sequence primer binding site and length stuffer at its 5 prime end. PCR amplification was carried out using +A/+CA AFLP amplification products of PSP11 and PI210234 prepared as described in example 4 as template. PCR conditions were as follows:
For 1 PCR reaction the following components were mixed:

| | |
|---|---|
| 5 µl 1/10 diluted AFLP mixture (app. 10 ng/µl) | |
| 5 µl 1 pmol/µl primer 1.2 f (diluted directly from a 500 µM stock) | |
| 5 µl 1 pmol/µl primer 1.2 r (diluted directly from a 500 µM stock) | |
| 5 µl PCR mix | 2 µl 10 x PCR buffer |
|  | 1 µl 5 mM dNTPs |
|  | 1.5 µl 25 mM MgCl$_2$ |
|  | 0.5 µl H$_2$O |
| 5 µl Enzyme mix | 0.5 µl 10 x PCR buffer (Applied Biosystems) |
|  | 0.1 µl 5U/µl AmpliTaq DNA polymerase (Applied Biosystems) |
|  | 4.4 µl H$_2$O |

The following PCR profile was used:

| | | |
|---|---|---|
| Cycle 1 | 2'; | 94° C. |
| Cycle 2-34 | 20"; | 94° C. |
|  | 30"; | 56° C. |
|  | 2'30"; | 72° C. |
| Cycle 35 | 7'; | 72° C. |
|  | ∞; | 4° C. |

PCR products were cloned into vector pCR2.1 (TA Cloning kit; Invitrogen) using the TA Cloning method and transformed into INVαF' competent *E. coli* cells. Transformants were subjected to blue/white screening. Three independent white transformants each for PSP11 and PI-201234 were selected and grown O/N in liquid selective medium for plasmid isolation.

Plasmids were isolated using the QIAprep Spin Miniprep kit (QIAGEN). Subsequently, the inserts of these plasmids were sequenced according to the protocol below and resolved on the MegaBACE 1000 (Amersham). Obtained sequences were inspected on the presence of the SNP allele. Two independent plasmids containing the PI-201234 insert and 1 plasmid containing the PSP11 insert contained the expected consensus sequence flanking the SNP. Sequence derived from the PSP11 fragment contained the expected A (underlined) allele and sequence derived from PI-201234 fragment contained the expected G allele (double underlined):

PSP11 (sequence 1): (5'-3')
[SEQ ID 35]
AAACCCAAACTCCCCCAATCGATTTCAAACCTAGAACA<u>A</u>TGTTGGTTTTG

GTGCTAACTTCAACCCCACTACTGTTTTGCTCTATTTTTGT

PI-201234 (sequence 1): (5'-3')
[SEQ ID 36]
AAACCCAAACTCCCCCAATCGATTTCAAACCTAGAACA<u>G</u>TGTTGGTTTTG

GTGCTAACTTCAACCCCACTACTGTTTTGCTCTATTTTTG

-continued

PI-201234 (sequence 2): (5'-3')

[SEQ ID 37]
AAACCCAAACTCCCCCAATCGATTTCAAACCTAGAACA<u>G</u>TGTTGGTTTTG

GTGCTAACTTCAACCCCACTACTGTTTGCTCTATTTTTG

This result indicates that the putative pepper A/G SNP represents a true genetic polymorphism detectable using the designed STS assay.

REFERENCES

1. Zabeau, M. and Vos, P. (1993) Selective restriction fragment amplification; a general method for DNA fingerprinting. EP 0534858-A1, B1, B2; U.S. Pat. No. 6,045,994.
2. Vos, P., Hogers, R., Bleeker, M., Reijans, M., van de Lee, T., Hornes, M., Frijters, A., Pot, J., Peleman, J., Kuiper, M. et al. (1995) AFLP: a new technique for DNA fingerprinting. *Nucl. Acids Res.*, 21, 4407-4414.
3. M. van der Meulen, J. Buntjer, M. J. T. van Eijk, P. Vos, and R. van Schaik. (2002). Highly automated AFLP fingerprint analysis on the MegaBACE capillary sequencer. *Plant, Animal and Microbial Genome X*, San Diego, Calif., January 12-16, P228, pp. 135.
4. Margulies et al., 2005. Genome sequencing in microfabricated high-density picoliter reactions. *Nature advanced online publication* 03959, August 1.
5. R. W. Michelmore, I. Paran, and R. V. Kesseli. (1991). Identification of markers linked to disease-resistance genes by bulked segregant analysis: a rapid method to detect markers in specific genomic regions by using segregating populations. Proc. Natl. Acad. Sci. USA 88(21):9828-32.
6. Shendure et al., 2005. Accurate multiplex polony sequencing of an evolved bacterial genome. *Scienceexpress Report*, August 4.

The invention claimed is:

1. A method for the discovery and genotyping of one or more genetic markers, comprising:

(a) ligating at least one adaptor to at least one DNA restriction fragment to produce at least one adaptor-ligated restriction fragment;

(b) amplifying by solution PCR the at least one adaptor-ligated restriction fragment with at least one primer pair to produce a library of at least one amplified adaptor-ligated double stranded restriction fragment, wherein the amplified adaptor-ligated restriction fragment comprises an identifier tag;

(c) sequencing a pool of two or more libraries of tagged amplified adaptor-ligated restriction fragments using high throughput sequencing technology, wherein each library comprises a unique identifier tag, wherein the sequencing comprises amplifying by PCR on a solid support;

(d) clustering the sequences per library, using the identifier tag; and (e) identifying genetic markers within the library and/or between libraries and determining dominant or co-dominant genotypes of the identified genetic markers in the two or more libraries.

2. The method according to claim 1, wherein the genetic marker is an AFLP marker or an SNP marker.

3. The method according to claim 1, wherein sequencing is based on sequencing by synthesis.

4. The method according to claim 1, wherein the sequencing comprises:

(c1) annealing amplified adaptor-ligated restriction fragments to beads, each bead annealing with a single adaptor-ligated fragment;
(c2) emulsifying the beads in water-in-oil microreactors, each water-in-oil microreactor comprising a single bead;
(c3) performing emulsion PCR to amplify the adaptor-ligated restriction fragments on the surface of the beads;
(c4) loading the beads in wells, each well comprising a single bead; and
(c5) generating a pyrophosphate signal.

5. The method according to claim 1, wherein the tagged amplified adaptor-ligated restriction fragments have an average sequencing redundancy of at least 6.

6. The method according to claim 1, wherein before the ligating step a size selection of DNA restriction fragments is performed by a denaturation step.

7. The method according to claim 1, wherein the DNA is selected from the group consisting of a genomic DNA, cDNA, BACs, YACs, whole-genome amplified DNA, and PCR product.

8. The method according to claim 1, wherein the adaptor is a double stranded synthetic oligonucleotide adaptor having one end that is compatible with one or both ends of the DNA restriction fragment.

9. The method according to claim 1, further comprising restricting one or more samples of DNA to produce the at least one DNA restriction fragment.

10. The method according to claim 9, wherein the DNA is restricted with two or more restriction endonucleases.

11. The method according to claim 10, wherein the DNA is restricted with two restriction endonucleases.

12. The method according to claim 10, wherein at least one of the restriction endonucleases is a rare cutter.

13. The method according to claim 10, wherein at least one of the restriction endonucleases is a frequent cutter.

14. The method according to claim 9, wherein the DNA is restricted using a combination of three or more restriction endonucleases.

15. The method according to claim 1, wherein the primer contains from 1 to 10 selective nucleotides.

16. The method according to claim 1, wherein the primer contains from 1 to 5 selective nucleotides.

17. The method according to claim 1, wherein determining a co-dominant genotype comprises co-dominant scoring of AFLP marker sequences.

18. The method according to claim 1, wherein determining a co-dominant genotype comprises co-dominant scoring of SNP marker sequences.

19. A method for genotyping one or more genetic markers, comprising:
(a) ligating at least one adaptor to at least one DNA restriction fragment to produce a library of at least one adaptor-ligated restriction fragment;
(b) sequencing a pool of two or more libraries of tagged adaptor-ligated restriction fragments using high throughput sequencing technology, wherein each library comprises a unique identifier tag, and wherein the sequencing comprises amplifying by PCR on a solid support;
(c) clustering the sequences per library, using the identifier tag; and
(d) identifying genetic markers within the library and/or between libraries and determining dominant or co-dominant genotypes of the identified genetic markers in the two or more libraries.

* * * * *